(12) United States Patent
Holton et al.

(10) Patent No.: US 6,191,287 B1
(45) Date of Patent: Feb. 20, 2001

(54) PROCESS FOR SELECTIVE DERIVATIZATION OF TAXANES

(75) Inventors: Robert A. Holton, Tallahassee, FL (US); Zhuming Zhang, Montclair, NJ (US); Paul A. Clarke, Tallahassee, FL (US)

(73) Assignee: Florida State University, Tallahassee, FL (US)

( * ) Notice: Under 35 U.S.C. 154(b), the term of this patent shall be extended for 0 days.

(21) Appl. No.: 09/335,408

(22) Filed: Jun. 17, 1999

Related U.S. Application Data

(62) Division of application No. 09/063,477, filed on Apr. 20, 1998
(60) Provisional application No. 60/056,000, filed on Aug. 18, 1997, and provisional application No. 60/081,265, filed on Apr. 9, 1998.

(51) Int. Cl.$^7$ .................................................. C07D 305/14
(52) U.S. Cl. ............................ 549/214; 549/510; 549/511
(58) Field of Search .................................... 549/214, 510, 549/511

(56) References Cited

U.S. PATENT DOCUMENTS

| | | | |
|---|---|---|---|
| Re. 34,277 | 6/1993 | Denis et al. | 549/510 |
| 4,857,653 | 8/1989 | Colin et al. | 549/511 |
| 4,960,790 | 10/1990 | Stella et al. | 514/449 |
| 5,136,060 | 8/1992 | Holton | 549/510 |
| 5,200,534 | 4/1993 | Rao | 549/510 |
| 5,254,703 | 10/1993 | Holton | 549/510 |
| 5,350,866 | 9/1994 | Holton et al. | 549/510 |
| 5,352,806 | 10/1994 | Gunawardana et al. | 549/510 |
| 5,367,086 | 11/1994 | Rao | 549/510 |
| 5,475,011 | 12/1995 | Ojima et al. | 514/320 |
| 5,478,854 | 12/1995 | Farina et al. | 514/374 |
| 5,489,601 | 2/1996 | Holton et al. | 514/337 |
| 5,594,157 | 1/1997 | Gunawardana et al. | 549/510 |
| 5,621,121 | 4/1997 | Commercon et al. | 549/510 |
| 5,646,176 | 7/1997 | Golik et al. | 514/444 |
| 5,688,977 | 11/1997 | Sisti et al. | 549/510 |
| 5,705,508 | 1/1998 | Ojima et al. | 514/320 |
| 5,714,513 | 2/1998 | Holton et al. | 514/449 |
| 5,750,736 | 5/1998 | Sisti | 549/510 |
| 5,773,461 | 6/1998 | Wittman et al. | 514/449 |
| 5,780,653 | 7/1998 | Tao et al. | 549/510 |
| 5,811,452 | 9/1998 | Ojima et al. | 514/449 |
| 5,874,595 | 2/1999 | Damen et al. | 549/510 |
| 5,914,411 | 6/1999 | Sisti et al. | 549/510 |

FOREIGN PATENT DOCUMENTS

| | | |
|---|---|---|
| 97/07110 | 8/1996 | (WO) . |
| 98/02427 | 7/1997 | (WO) . |
| 99/09021 | 2/1999 | (WO) . |

OTHER PUBLICATIONS

Holton et al., "Selective Protection of the C(7) and C(10) Hydroxyl Groups in 10–Deacetyl Baccatin III", Tetrahedron Letters, vol. 329 (1998) pp. 2883–2886.

Denis, J. N. et al., "A Highly Efficient, Practical Approach to Natural Taxol", J. Am. Chem. Soc., vol. 110 (1988) pp. 5917–5919.

*Primary Examiner*—Ba K. Trinh
(74) *Attorney, Agent, or Firm*—Senniger, Powers, Leavitt & Roedel

(57) ABSTRACT

Processes for the preparation of taxol and other taxanes through selective derivatization of the C(7) and C(10) hydroxyl groups of 10-DAB, particularly a novel process using a new strategy in which the C(10) hydroxyl group is protected or derivatized prior to the C(7) hydroxyl group; and the provision of C(7) and C(10) derivatized 10-DAB compounds.

9 Claims, No Drawings

PROCESS FOR SELECTIVE DERIVATIZATION OF TAXANES

This application is a divisional application of U.S. Ser. No. 09/063,477, filed Apr. 20, 1998, which claims priority from provisional application Ser. No. 60/081,265, filed Apr. 9, 1998 and Ser. No. 60/081,265, filed Aug. 18, 1997.

This invention was made with Government support under NIH Grant #CA 42031 awarded by the National Institutes of Health. The Government has certain rights in the invention.

BACKGROUND OF THE INVENTION

The present invention is directed, in general, to a process for the preparation of taxol and other taxanes, and in particular, to such a process in which the C(7) or C(10) hydroxyl group of a taxane is selectively derivatized.

10-DAB (1), which is extracted from the needles of taxus baccata L., the English yew, has become a key starting material in the production of taxol and Taxotere, both of which are potent anticancer agents. Conversion of 10-DAB to taxol, Taxotere® and other taxanes having antitumor activity requires protection or derivatization of the C(7) and C(10) hydroxyl groups followed by esterification of the C(13) hydroxyl group to attach an appropriate side chain at that position.

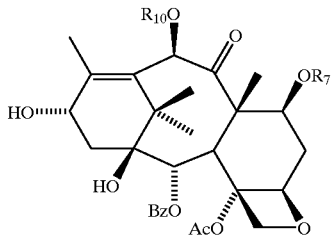

1 $R_{10} = R_7 = H$
2 $R_{10} = H, R_7 = TES$

Until now, strategies for the preparation of taxol and taxol analogs were based upon the observation of Senilh et al. (*C.R. Acad. Sci. Paris, IT*, 1981, 293, 501) that the relative reactivity of the four hydroxyl groups of 10-DAB toward acetic anhydride in pyridine is C(7)—OH>C(10)—OH>C(13)—OH>C(1)—OH. Denis, et. al. reported (*J. Am. Chem. Soc.*, 1988, 110, 5917) selective silylation of the C(7) hydroxyl group of 10-DAB with triethylsilyl chloride in pyridine to give 7-triethylsilyl-10-deacetyl baccatin (III) (2) in 85% yield. Based upon these reports, in those processes in which differentiation of the C(7) and C(10) hydroxyl groups is required (e.g., preparation of taxol from 10-DAB), the C(7) hydroxyl group must be protected (or derivatized) before the C(10) hydroxyl group is protected or derivatized. For example, taxol may be prepared by treating 10-DAB with triethylsilyl chloride to protect the C(7) hydroxyl group, acetylating the C(10) hydroxyl group, attaching the side chain by esterification of the C(13) hydroxyl group, and, finally, removal of protecting groups.

It is known that taxanes having various substituents bonded to either the C(10) or the C(7) oxygens show anticancer activity. To provide for more efficient synthesis of these materials, it would be useful to have methods which permit more efficient and more highly selective protection or derivatization of the C(10) and the C(7) hydroxyl groups.

SUMMARY OF THE INVENTION

Among the objects of the present invention, therefore, is the provision of highly efficient processes for the preparation of taxol and other taxanes through selective derivatization of the C(7) group or the C(10) hydroxyl group of 10-DAB and other taxanes, particularly a process in which the C(10) hydroxyl group is protected or derivatized prior to the C(7) hydroxyl group; and the provision of C(7) or C(10) derivatized taxanes.

Briefly, therefore, the present invention is directed to a process for the acylation of the C(10) hydroxy group of a taxane. The process comprises forming a reaction mixture containing the taxane and an acylating agent which contains less than one equivalent of an amine base for each equivalent of taxane, and allowing the taxane to react with the acylating agent to form a C(10) acylated taxane.

The present invention is further directed to a process for the silylation of the C(10) hydroxy group of a taxane having a C(10) hydroxy group. The process comprises treating the taxane with a silylamide or a bissilylamide to form a C(10) silylated taxane.

The present invention is further directed to a process for converting the C(7) hydroxy group of a 10-acyloxy-7-hydroxytaxane to an acetal or ketal. The process comprises treating the 10-acyloxy-7-hydroxytaxane with a ketalizing agent in the presence of an acid catalyst to form a C(10) ketalized taxane.

The present invention is further directed to a taxane having the structure:

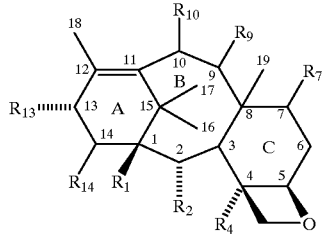

wherein
M is a metal or comprises ammonium:
$R_1$ is hydrogen, hydroxy, protected hydroxy, or together with $R_{14}$ or $R_2$ forms a carbonate;
$R_2$ is keto, —$OT_2$, acyloxy, or together with $R_1$ forms a carbonate;
$R_4$ is —$OT_4$ or acyloxy;
$R_7$ is —$OSiR_JR_KR_L$;
$R_9$ is hydrogen, keto, —$OT_9$, or acyloxy;
$R_{10}$ is hydrogen, keto, —$OT_{10}$, or acyloxy;
$R_{13}$ is hydroxy, protected hydroxy, keto, or MO—;
$R_{14}$ is hydrogen, —$OT_{14}$, acyloxy, or together with $R_1$ forms a carbonate;
$R_J$, $R_K$, $R_L$ are independently hydrocarbyl, substituted hydrocarbyl, or heteroaryl, provided, however, if each of $R_J$, $R_K$ and $R_L$ are alkyl, at least one of $R_J$, $R_K$ and $R_L$ comprises a carbon skeleton having at least four carbon atoms; and
$T_2$, $T_4$, $T_9$, $T_{10}$, and $T_{14}$ are independently hydrogen or hydroxy protecting group.

Other objects and features of this invention will be in part apparent and in part pointed out hereinafter.

DETAILED DESCRIPTION OF THE PREFERRED EMBODIMENTS

Among other things, the present invention enables the selective derivatization of the C(10) hydroxyl group of a taxane without first protecting the C(7) hydroxyl group. Stated another way, it has been discovered that the reactivities previously reported for the C(7) and C(10) hydroxyl groups can be reversed, that is, the reactivity of the C(10) hydroxyl group becomes greater than the reactivity of the C(7) hydroxyl group under certain conditions.

Although the present invention may be used to selectively derivatize a taxane having a hydroxy group at C(7) or C(10), it offers particular advantages in the selective derivatization of taxanes having hydroxy groups at C(7) and C(10), i.e., 7,10-dihydroxy taxanes. In general, 7,10-dihydroxytaxanes which may be selectively derivatized in accordance with the present invention correspond to the following structure:

3 wherein
$R_1$ is hydrogen, hydroxy, protected hydroxy, or together with $R_{14}$ or $R_2$ forms a carbonate;
$R_2$ is keto, $-OT_2$, acyloxy, or together with $R_1$ forms a carbonate;
$R_4$ is $-OT_4$ or acyloxy;
$R_9$ is hydrogen, keto, $-OT_9$, or acyloxy;
$R_{13}$ is hydroxy, protected hydroxy, keto, or $R_{14}$ is hydrogen, $-OT_{14}$, acyloxy or together with $R_1$ forms a carbonate;
$T_2$, $T_4$, $T_9$, and $T_{14}$ are independently hydrogen or hydroxy protecting group;
$X_1$ is $-OX_6$, $-SX_7$, or $-NX_8X_9$;
$X_2$ is hydrogen, hydrocarbyl, substituted hydrocarbyl, or heteroaryl;
$X_3$ and $X_4$ are independently hydrogen, hydrocarbyl, substituted hydrocarbyl, or heteroaryl;
$X_5$ is $-X_{10}$, $-OX_{10}$, $-SX_{10}$, $-NX_8X_{10}$ or $-SO_2X_{11}$;
$X_6$ is hydrocarbyl, substituted hydrocarbyl, heteroaryl, hydroxy protecting group or a functional group which increases the water solubility of the taxane derivative;
$X_7$ is hydrocarbyl, substituted hydrocarbyl, heteroaryl, or sulfhydryl protecting group;
$X_8$ is hydrogen, hydrocarbyl, or substituted hydrocarbyl;
$X_9$ is an amino protecting group;
$X_{10}$ is hydrocarbyl, substituted hydrocarbyl, or heteroaryl;
$X_{11}$ is hydrocarbyl, substituted hydrocarbyl, heteroaryl, $-OX_{10}$, or $-NX_8X_{14}$; and
$X_{14}$ is hydrogen, hydrocarbyl, substituted hydrocarbyl, or heteroaryl.

Selective C(10) Derivatization

In accordance with the process of the present invention, it has been discovered that the C(10) hydroxyl group of a taxane can be selectively acylated in the absence of an amine base. Preferably, therefore, amine bases such as pyridine, triethylamine, dimethylaminopyridine and 2,6-lutidine, if present at all, are present in the reaction mixture in relatively low concentration. Stated another way, if an amine base is present in the reaction mixture, the molar ratio of the amine base to the taxane is preferably less than 1:1, more preferably less than 10:1, and most preferably less than 100:1.

Acylating agents which may be used for the selective acylation of the C(10) hydroxyl group of a taxane include anhydrides, dicarbonates, thiodicarbonates, and isocyanates. In general, the anhydrides, dicarbonates, and thiodicarbonates correspond to structure 4 and the isocyanates correspond to structure 5:

4

5

$R^3-N=C=O$ wherein $R^1$ is $-OR^a$, $-SR^a$, or $R^a$; $R^2$ is $-OC(O)R^b$, $-OC(O)OR^b$, $-OC(O)SR^b$, $-OPOR^bR^c$, or $-OS(O)_2R^b$; $R^3$ is hydrocarbyl, substituted hydrocarbyl, or heteroaryl; and $R^a$, $R^b$, $R^c$ are independently hydrocarbyl, substituted hydrocarbyl, or heteroaryl. For example, suitable carboxylic acid anhydride acylating agents include acetic anhydride, chloroacetic anhydride, propionic anhydride, benzoic anhydride, and other carboxylic acid anhydrides containing substituted or unsubstituted hydrocarbyl or heteroaryl moieties; suitable dicarbonate acylating reagents include dibenzyl dicarbonate, diallyl dicarbonate, dipropyl dicarbonate, and other dicarbonates containing substituted or unsubstituted hydrocarbyl or heteroaryl moieties; and suitable isocyanate acylating agents include phenyl isocyanate, and other isocyanates containing substituted or unsubstituted hydrocarbyl or heteroaryl moieties. In addition, although the anhydrides, dicarbonates, and thiodicarbonates used as acylating agents may be mixed, it is generally preferred that they be symmetrical; that is, $R^1$ and $R^2$ are selected such that the molecule is symmetrical (e.g., if $R^1$ is $R^a$, $R^2$ is $-OC(O)R^b$ with $R^a$ being the same as $R^b$).

While the acylation of the C(10) hydroxy group of the taxane will proceed at an adequate rate for many acylating agents, it has been discovered that the reaction rate may be increased by including a Lewis acid in the reaction mixture. The concentration of the Lewis acid appears not to be narrowly critical; experimental evidence obtained to date suggests it may be present in either a stoichiometric or a catalytic amount. In general, Lewis acids which may be used include triflates and halides of elements of groups IB, IIB, IIIB, IVB, VB, VIB, VIIB, VIII, IIIA, IVA, lanthanides, and actinides of the Periodic Table (American Chemical Society format). Preferred Lewis acids include zinc chloride, stannic chloride, cerium trichloride, cuprous chloride, lanthanum trichloride, dysprosium trichloride, and ytterbium trichloride. Zinc chloride or cerium trichloride is particularly preferred when the acylating agent is an anhydride or dicarbonate. Cuprous chloride is particularly preferred when the acylating agent is an isocyanate.

The solvent for the selective acylation is preferably an ethereal solvent such as tetrahydrofuran. Alternatively, however, other solvents such as ether or dimethoxyethane may be used.

The temperature at which the C(10) selective acylation is carried out is not narrowly critical. In general, however, it is preferably carried out at room temperature or higher in order for the reaction to proceed at a sufficiently high rate.

For purposes of illustration, acylating reactions involving dibenzyl dicarbonate, diallyl dicarbonate, acetic anhydride, chloroacetic anhydride and phenyl isocyanate are illustrated in Reaction Schemes 1 through 5 below. In this series of reaction schemes, the taxane which is selectively acylated at the C(10) position is 10-deacetylbaccatin III. It should be understood, however, that these reaction schemes are merely illustrative and that other taxanes having a C(10) hydroxy group, in general, and other 7,10-dihydroxytaxanes, in particular, may be selectively acylated with these and other acylating agents in accordance with the present invention.

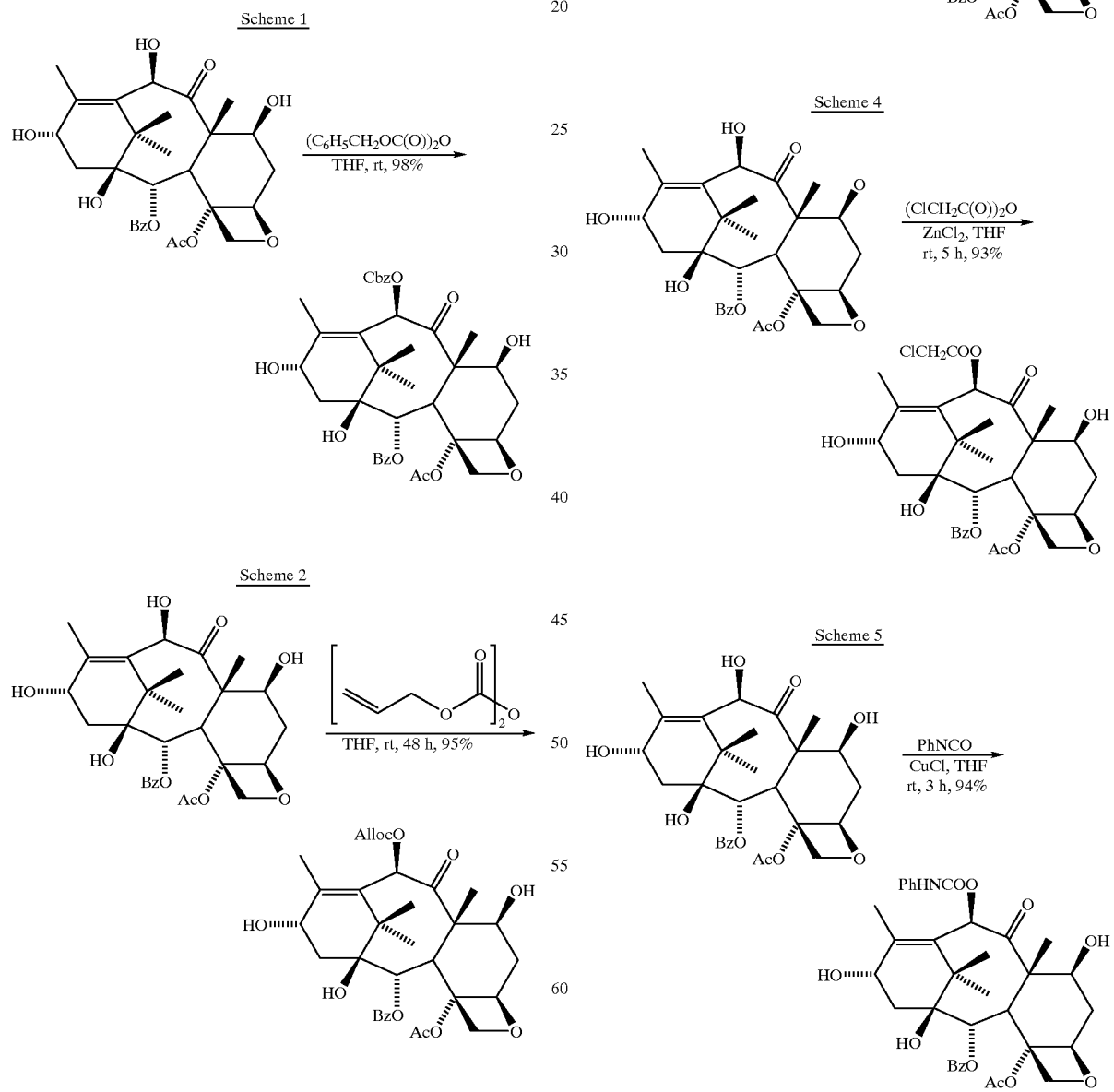

In another aspect of the present invention, the C(10) hydroxyl group of a taxane may be selectively silylated. In general, the silylating agent is selected from the group consisting of silylamides and bissilyamides. Preferred silylamides and bissilyamides correspond to structures 6 and 7, respectively:

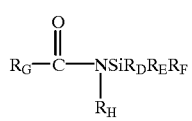

6

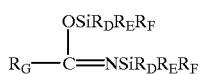

7 trifluoromethylacetamides and bis tri(hydrocarbyl) silyltrifluoromethylacetamides, with the hydrocarbyl moiety being substituted or unsubstituted alkyl or aryl. For example, the preferred silylamides and bissilyamides include N,O-bis-(trimethylsilyl) trifluoroacetamide, N,O-bis-(triethylsilyl)trifluoroacetamide, N-methyl-N-triethylsilyltrifluoroacetamide, and N,O-bis(t-butyldimethylsilyl)trifluoroacetamide.

The silylating agents may be used either alone or in combination with a catalytic amount of a base such as an alkali metal base. Alkali metal amides, such as lithium amide catalysts, in general, and lithium hexamethyldisilazide, in particular, are preferred.

The solvent for the selective silylation reaction is preferably an ethereal solvent such as tetrahydrofuran. Alternatively, however, other solvents such as ether or dimethoxyethane may be used.

The temperature at which the C(10) selective silylation is carried out is not narrowly critical. In general, however, it is carried out at 0° C. or greater.

Selective C(10) silylation reactions involving N,O-bis (trimethylsilyl)trifluoroacetamide and N,O-bis(triethylsilyl) trifluoroacetamide are illustrated in Reaction Schemes 6 and 7 below. In these reaction schemes, the taxane which is selectively silylated at the C(10) position is 10-deacetylbaccatin III. It should be understood, however, that these reaction schemes are merely illustrative and that other taxanes, having a C(10) hydroxy group, in general, and other 7,10-dihydroxytaxanes, in particular, may be selectively silylated with these and other silylating agents in accordance with the present invention.

Scheme 6

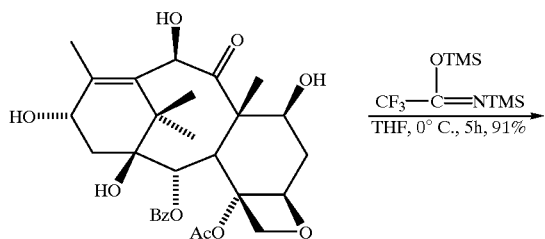

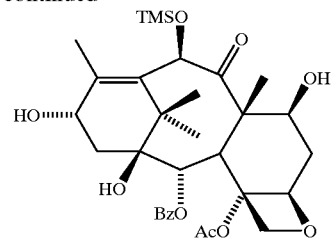

Scheme 7

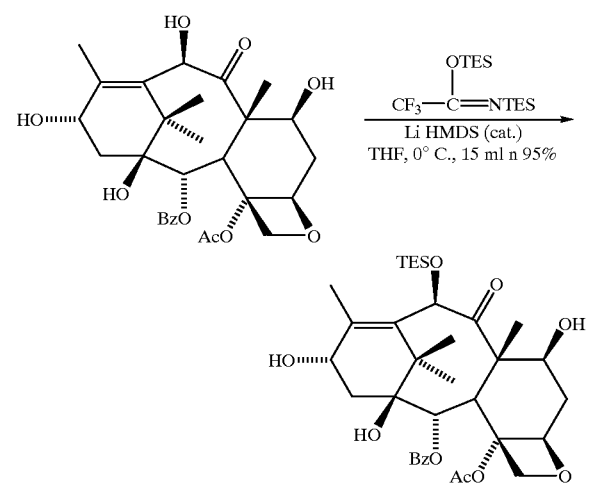

After the C(10) hydroxyl group of a 7,10-dihydroxytaxane has been derivatized as described herein, the C(7) hydroxyl group can readily be protected or otherwise derivatized selectively in the presence of the C(1) and C(13) hydroxyl groups (and a C(14) hydroxy group, if present).

Selective C(7) Derivatization

Selective acylation of the C(7) hydroxyl group of a C(10) acylated or silylated taxane can be achieved using any of a variety of common acylating agents including, but not limited to, substituted and unsubstituted carboxylic acid derivatives, e.g., carboxylic acid halides, anhydrides, dicarbonates, isocyanates and haloformates. For example, the C(7) hydroxyl group of baccatin III, 10-acyl-10-deacetylbaccatin III or 10-trihydrocarbylsilyl-10-deacetyl baccatin III can be selectively acylated with dibenzyl dicarbonate, diallyl dicarbonate, 2,2,2-trichloroethyl chloroformate, benzyl chloroformate or another common acylating agent.

In general, acylation of the C(7) hydroxy group of a C(10) acylated or silylated taxane are more efficient and more selective than are C(7) acylations of a 7,10-dihydroxy taxane such as 10-DAB, i.e., once the C(10) hydroxyl group has been acylated or silylated, there is a significant difference in the reactivity of the remaining C(7), C(13), and C(1) hydroxyl groups (and the C(14) hydroxyl group, if present). These acylation reactions may optionally be carried out in the presence or absence of an amine base.

Examples of selective C(7) acylation of a taxane having an acylated or silylated C(10) hydroxy group are shown in Reaction Schemes 8 through 11. In these reaction schemes, the taxane which is selectively acylated at the C(7) position is baccatin III or 10-triethylsilyl-10-deacetylbaccatin III. It should be understood, however, that these reaction schemes are merely illustrative and that taxanes having other acyl and silyl moieties at C(10) as well as other substituents at other taxane ring positions may be selectively acylated at C(7) with these and other acylating agents in accordance with the present invention.

Scheme 8

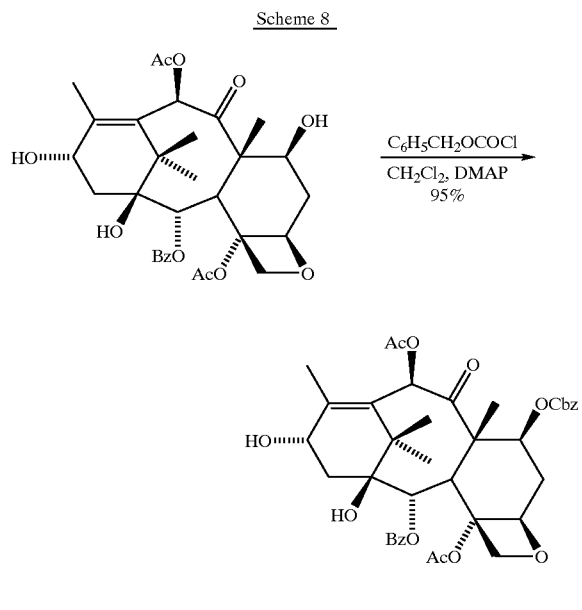

Scheme 9

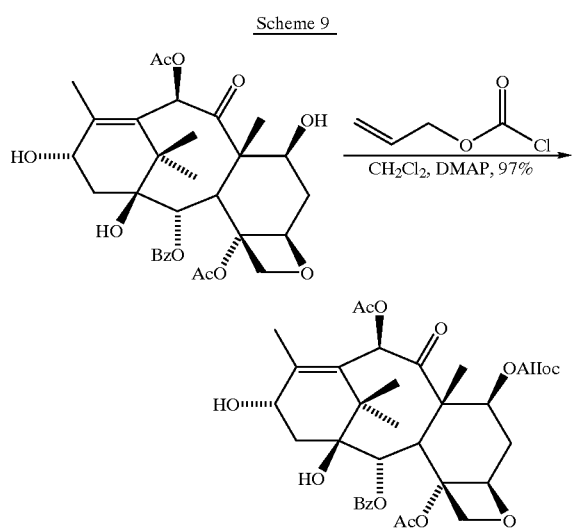

Scheme 10

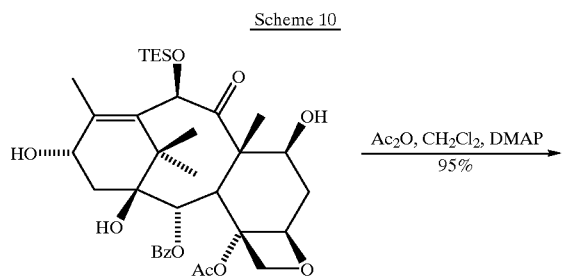

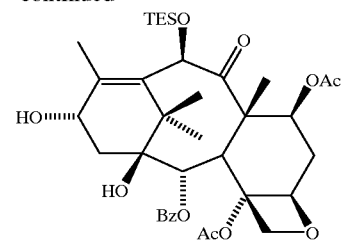

Scheme 11

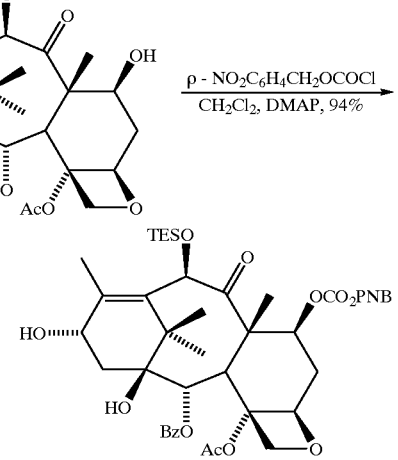

Alternatively, the C(7) hydroxyl group of a C(10) acylated taxane derivative can be selectively protected using any of a variety of hydroxy protecting groups, such as acetal, ketal, silyl, and removable acyl protecting groups. For example, the C(7) hydroxyl group may be silylated using any of a variety of common silylating agents including, but not limited to, tri(hydrocarbyl)silyl halides and tri(hydrocarbyl) silyl triflates. The hydrocarbyl moieties of these compounds may be substituted or unsubstituted and preferably are substituted or unsubstituted alkyl or aryl. For example, the C(7) hydroxyl group of baccatin III can be selectively silylated using silylating agents such as tribenzylsilyl chloride, trimethylsilyl chloride, triethylsilyl chloride, dimethyl isopropylsilyl chloride, dimethyl phenylsilyl chloride, and the like.

In general, silylations of the C(7) hydroxy group of a C(10) acylated taxanes are more efficient and more selective than are silylations of a 7,10-dihydroxy taxane such as 10-DAB, i.e., once the C(10) hydroxyl group has been acylated, there is a significant difference in the reactivity of the remaining C(7), C(13), and C(1) hydroxyl groups (and the C(14) hydroxyl group, if present). The C(7) silylation reaction may be carried out under a wide range of conditions, including in the presence or absence of an amine base.

Examples of selective C(7) silylation of C(10) acylated taxanes are shown in Reaction Schemes 12 through 15. In these reaction schemes, the taxane which is selectively silylated at the C(7) position is baccatin III or another C(10)-acyloxy derivative of 10-deacetylbaccatin III. It should be understood, however, that these reaction schemes are merely illustrative and that other taxanes may be selectively silylated with these and other silylating agents in accordance with the present invention.

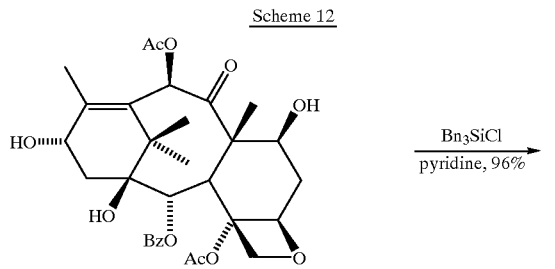

Alternatively, the C(7) hydroxyl group of C(10) acylated taxanes can be selectively protected using any of a variety of common reagents including, but not limited to, simple acetals, ketals and vinyl ethers, in the presence of an acid catalyst. These reagents (whether acetal, ketal, vinyl ether or otherwise) are referred to herein as "ketalizing agents" and are described in "Protective Groups in Organic Synthesis" by T. W. Greene, John Wiley and Sons, 1981. The acid catalyst used may be an organic or inorganic acid, such as toluenesulfonic acid or camphorsulfonic acid, in at least a catalytic amount. For example, the C(7) hydroxyl group of baccatin III can be selectively ketalized using 2-methoxy propene. Other suitable reagents for the preparation of acetals and ketals include methyl vinyl ether, ethyl vinyl ether, tetrahydropyran, and the like.

Selective ketalization of the C(7) substituent of a C(10) acylated taxane is more efficient and more selective than it is with 10-DAB, i.e., once the C(10) hydroxyl group has been acylated, there is a large difference in the reactivity of the remaining C(7), C(13), and C(1) hydroxyl groups (and the C(14) hydroxyl group, if present).

An example of selective formation of a C(7) ketal from baccatin III is illustrated in Reaction Scheme 16. It should be understood, however, that this reaction scheme is merely illustrative and that other taxanes may be selectively ketalized with this and other ketalizing agents in accordance with the present invention.

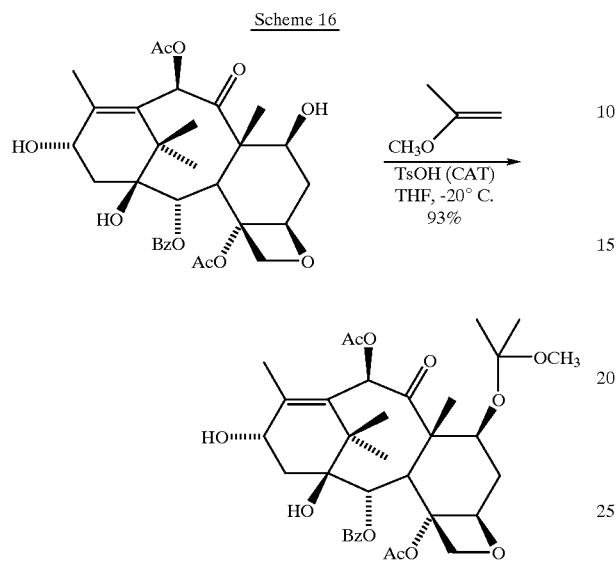

Scheme 16

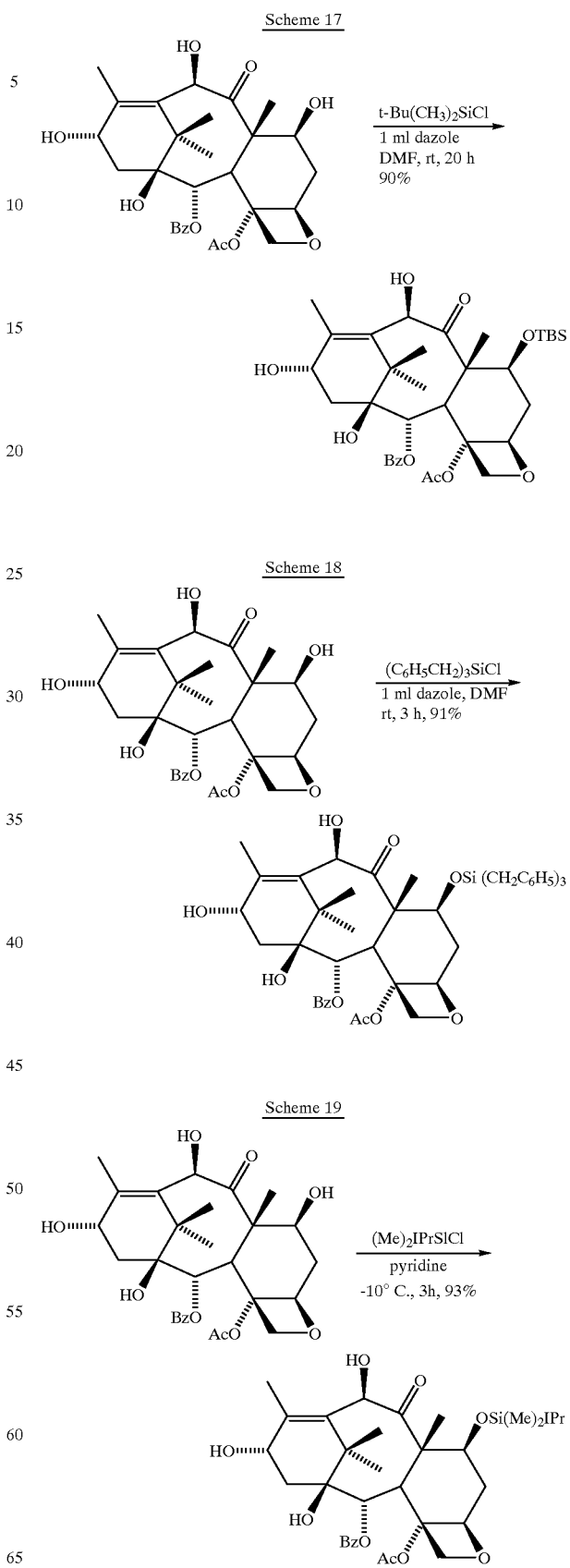

Scheme 17

Scheme 18

Scheme 19

Under appropriate conditions, the C(7) hydroxyl group of a taxane further comprising a C(10) hydroxyl group can be selectively silylated. Advantageously, these silylations are not limited to silyl groups bearing alkyl substituents having three carbons or less.

In general, the C(7) hydroxyl group of a taxane can be selectively silylated with a silylating agent which includes the —SiR$_J$R$_K$R$_L$ moiety wherein R$_J$, R$_K$ and R$_L$ are independently substituted or unsubstituted hydrocarbyl or heteroaryl, provided that any substituents are other than hydroxyl. In one embodiment of the present invention, if each of R$_J$, R$_K$ and R$_L$ is alkyl, then at least one of R$_J$, R$_K$, and R$_L$ comprises a carbon skeleton (i.e., carbon chain or ring(s)) having at least four carbon atoms. Suitable silylating agents include silyl halides and silyl triflates, for example, tri(hydrocarbyl)silyl halides and tri(hydrocarbyl)silyl triflates. The hydrocarbyl substituents of these silylating agents may be substituted or unsubstituted and preferably are substituted or unsubstituted alkyl or aryl.

The selective silylation of the C(7) hydroxy group may be carried out in a solvent, such as dimethyl formamide ("DMF") or pyridine and in the presence of an amine base, such as imidazole or pyridine. Reaction Schemes 17–20 illustrate the silylation of the C(7) hydroxy group of 10-DAB in high yield by treating 10-DAB with t-butyldimethylsilyl chloride, tribenzylsilyl chloride, dimethyl-isopropylsilyl chloride, and dimethylphenylsilyl chloride, respectively. Silylation under these conditions was surprising in view of the report by Denis, et. al. (*J. Am. Chem. Soc.*, 1988, 110, 5917) that selective formation of 7-TBS-10-DAB was not possible.

Scheme 20

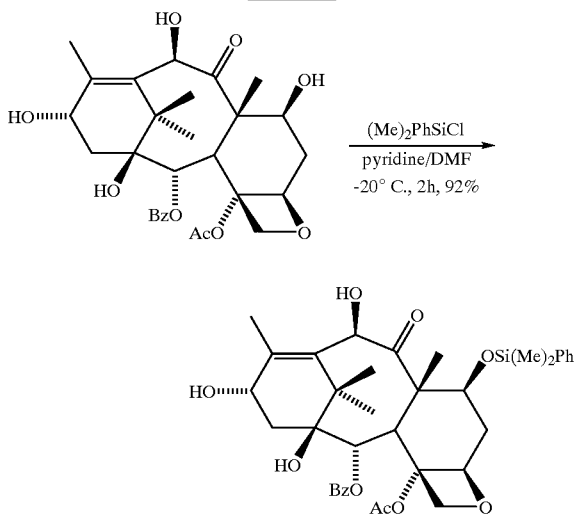

The process of the present invention can also be used to protect the C(7) and C(10) hydroxy groups of a 7,10-dihydroxytaxane with different silyl protecting groups. By selecting groups which can be removed under different conditions, the C(7) and C(10) hydroxy groups can be separately accessed for derivatization. These reactions, therefore, increase the flexibility of the overall process and, enable a higher yield for many of the individual protecting reactions relative to the yield obtained using currently available processes. For example, the triethylsilyl protecting group is more readily removed from C(10) than is the t-butyldimethylsilyl protecting group from C(7) and the dimethylphenylsilyl protecting group is more readily removed from C(7) than is the t-butyldimethylsilyl protecting group from C(10). The preparation of 7-t-butyldimethylsilyl-10-triethylsilyl-10-DAB and 7-dimethylphenylsilyl-10-t-butyldimethylislyl-10-DAB are illustrated in Reaction Schemes 21 and 22.

Scheme 21

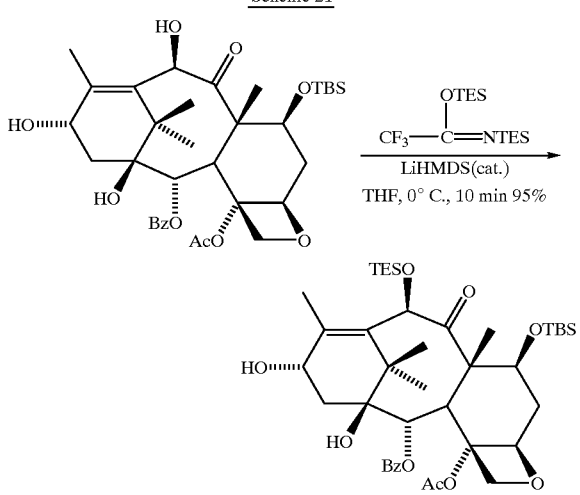

Scheme 22

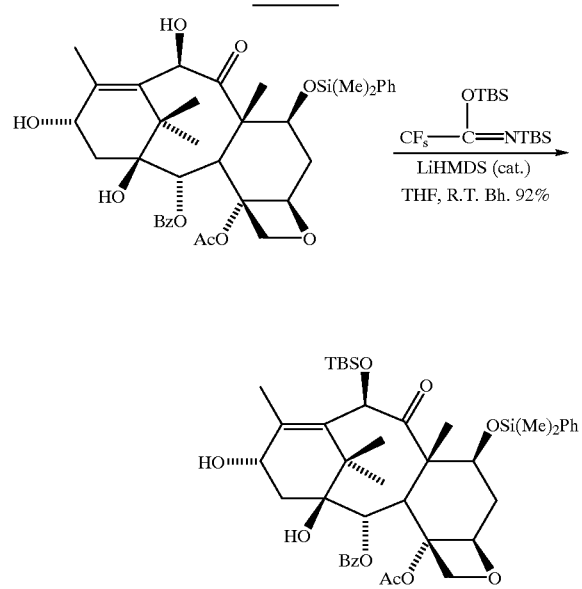

The methods disclosed herein may be used in connection with a large number of different taxanes obtained from natural or synthetic sources to prepare a wide variety of taxane intermediates which may then be further derivatized. For example, the methods of the present invention may be effectively used to protect the C(7) and/or C(10) hydroxy functional group prior to the coupling reaction between a C(13) side chain precursor and a taxane to introduce a C(13) β-amido ester side chain, and also prior to the reactions for preparing taxanes having alternative substituents at various locations on the taxane nucleus.

The attachment of a C(13) side chain precursor to a taxane may be carried out by various known techniques. For example, a side chain precursor such as an appropriately substituted β-lactam, oxazoline, oxazolidine carboxylic acid, oxazolidine carboxylic acid anhydride, or isoserine derivative may be reacted with a tricyclic or tetracyclic taxane having a C(13) hydroxy, metallic oxide or ammonium oxide substituent to form compounds having a β-amido ester substituent at C(13) as described, for example, Taxol: Science and Applications, M. Suffness, editor, CRC Press (Boca Rotan, Fla.) 1995, Chapter V, pages 97–121. For example, the synthesis of taxol from 10-DAB is illustrated in reaction scheme 23. It should be noted that while a β-lactam and 10-DAB are used in this reaction scheme, other side chain precursors and other taxanes could be substituted therefor without departing from the present invention.

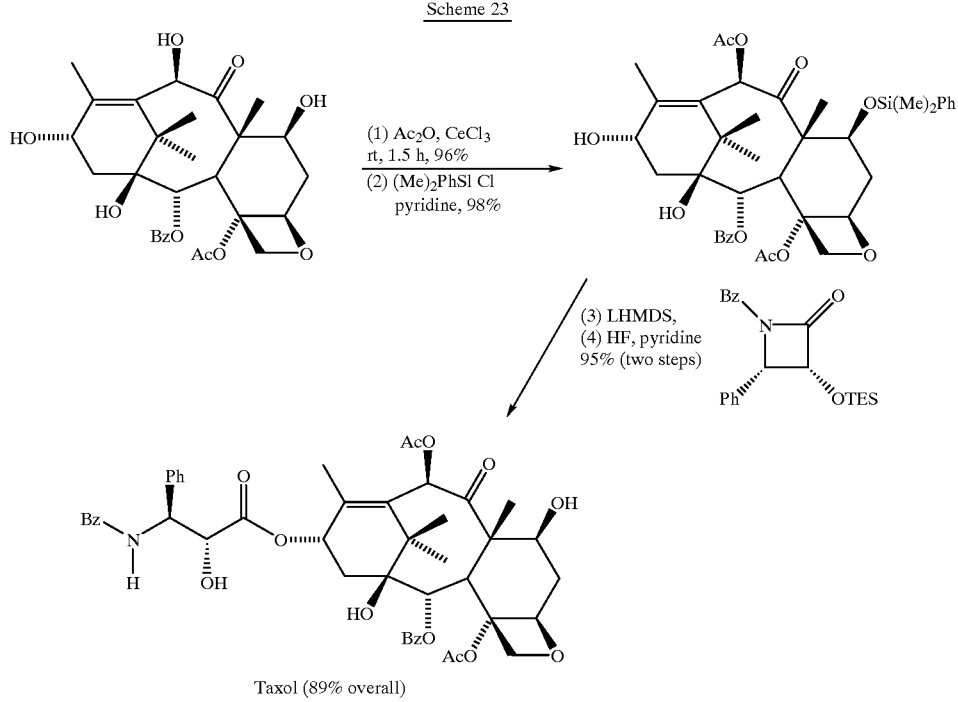

The process illustrated in Reaction Scheme 23 is significantly more efficient than any other currently known process, due to the high yields and selectivity of the cerium trichloride catalyzed acetylation of the C(10) hydroxyl group of 10-DAB and the subsequent silylation of the C(7) hydroxyl group. The synthesis proceeds in four steps and 89% overall yield.

Reaction schemes 24 and 25 illustrate the preparation of taxanes having substituents appended to the C(7) hydroxyl group and a free C(10) hydroxyl group. The method of the current invention provides flexibility so that the substituent attached to the C(7) hydroxyl group can be put in place either before or after attachment of the C(13) side chain.

Reaction scheme 24 outlines the preparation of a taxane which has been found to be a potent chemotherapeutic radiosensitizer, illustrating attachment of the substituent at the C(7) hydroxyl group before introduction of the C(13) side chain. According to the process of reaction scheme 7, 10-DAB is first converted to 10-TES-10-DAB. The C(7) hydroxyl group is then converted to an intermediate imidazolide by treatment with carbonyl diimidazole, and the intermediate imidazolide subsequently reacts, without isolation, with metronidazole alcohol to provide 7-metro-10-TES-10-DAB. Coupling of 7-metro-10-TES-10-DAB with a β-lactam to introduce the side chain at C(13) is followed by removal of the TES groups at C(10) and C(2') by treatment with HF and pyridine.

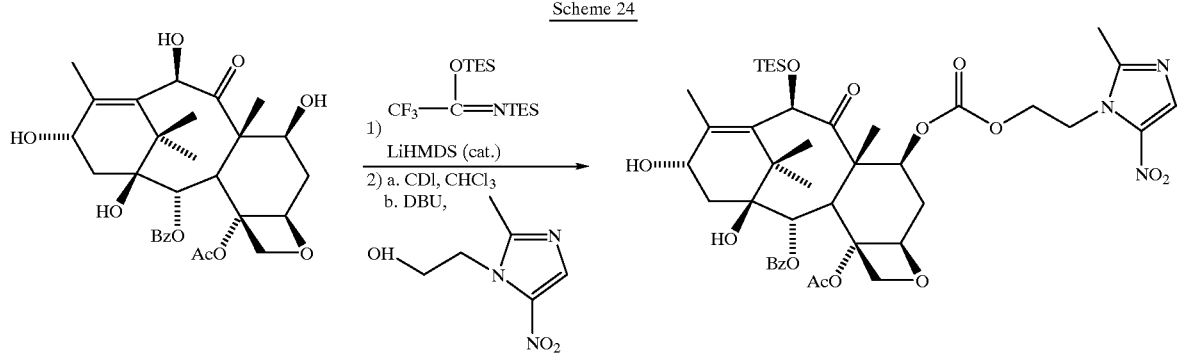

-continued

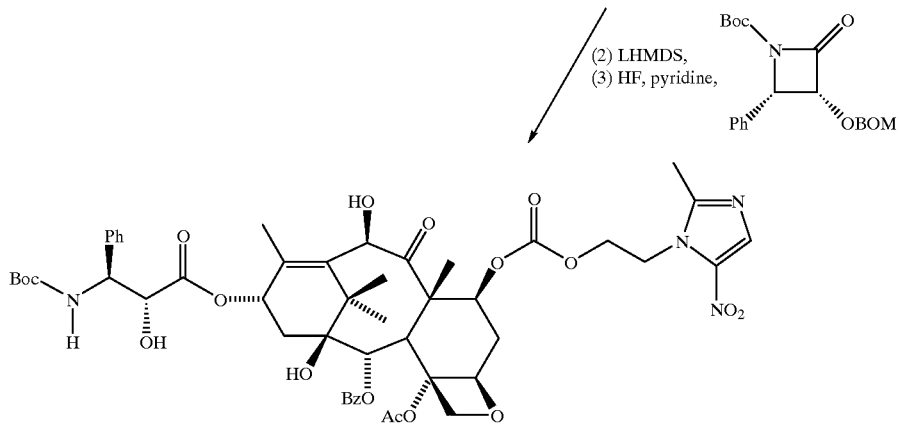

Reaction scheme 25 outlines the preparation of a taxane useful in identifying proteins which form bioconjugates with taxanes. It illustrates a protocol for attachment of a substituent at the C(7) hydroxyl group after introduction of the C(13) side chain. According to the processes of reaction schemes 7 and 11, 10-DAB is first converted to 7-p-nitrobenzyloxycarbonyl-10-TES-10-DAB. The C(13) side chain is attached employing a TES protected β-lactam, and the p-nitrobenzyloxycarbonyl protecting group is then selectively removed by treatment with hydrogen and a palladium catalyst, producing 2',10-(bis)-TES-taxotere. The C(7) hydroxyl group then reacts with carbonyl diimidazole and the derived imidazolide is treated with 1,4-diamino butane to give a primary amine. Reaction of the primary amine with the hydroxysuccinimide ester of biotin completes the attachment of the biotinamide group at C(7). Finally, treatment with HF in pyridine solution removes the TES protecting groups at C(10) and C(2').

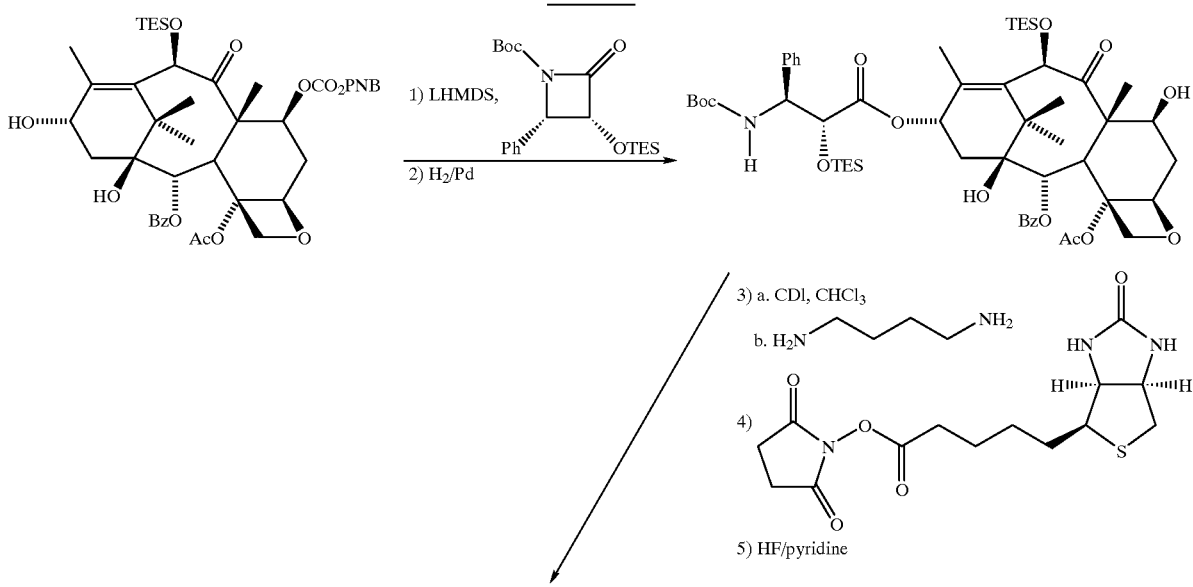

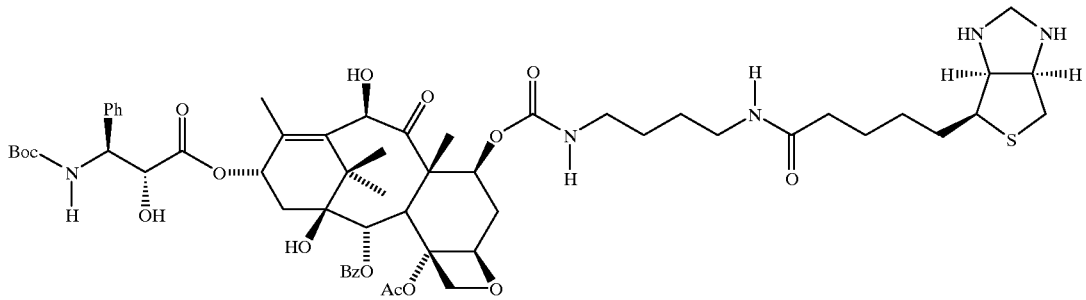

-continued

The protected taxane derivatives or the intermediates or starting materials used in the preparation of such protected taxane derivatives can be further modified to provide for alternative substituents at various positions of the taxane.

Taxanes having C(2) and/or C(4) substituents other than benzoyloxy and acetoxy, respectively, can be prepared from baccatin III, 10-DAB and other taxanes as more fully described in PCT Patent Application WO 94/01223. In general, the C(2) and C(4) acyloxy substituents are treated with lithium aluminum hydride or another suitable reducing agent to from hydroxy groups at C(2) and C(4) which may then be reacted, for example, with carboxylic acid halides (optionally after protection of the C(2) hydroxy group together with the C(1) hydroxy group with a 1,2-carbonate protecting group) to obtain the desired C(2) and C(4) derivatives.

Taxanes having C(7) substituents other than hydroxy and acyloxy as described herein can be prepared from baccatin III, 10-DAB, and other taxanes as more fully described in PCT Patent Application WO 94/17050. For example, a C(7) xanthate may be subjected to tin hydride reduction to yield the corresponding C(7) dihydro taxane. Alternatively, C(7) fluoro-substituted taxanes can be prepared by treatment of C(13)-triethylsilyl-protected baccatin III with 2-chloro-1,1,2-trifluorotriethylamine at room temperature in THF solution. Other baccatin derivatives with a free C(7) hydroxyl group behave similarly. Alternatively, 7-chloro baccatin III can be prepared by treatment of baccatin III with methanesulfonyl chloride and triethylamine in methylene chloride solution containing an excess of triethylamine hydrochloride.

Taxanes having C(9) substituents other than keto can be prepared from baccatin III, 10-DAB and other taxanes as more fully described in PCT Patent Application WO 94/20088. In general, the C(9) keto substituent of the taxane is selectively reduced to yield the corresponding C(9) β-hydroxy derivative with a borohydride, preferably tetrabutylammonium borohydride ($Bu_4NBH_4$) or triacetoxyborohydride. The C(9) β-hydroxy derivative can then be protected at C(7) with a hydroxy protecting group and the C(9) hydroxy group can be acylated following the methods described herein for acylation of the C(7) hydroxy group. Alternatively, reaction of 7-protected-9β-hydroxy derivative with KH causes the acetate group (or other acyloxy group) to migrate from C(10) to C(9) and the hydroxy group to migrate from C(9) to C(10), thereby yielding a 10-desacetyl derivative, which can be acylated as described elsewhere herein.

Taxanes having C(10) substituents other than hydroxy, acyloxy or protected hydroxy as described herein may be prepared as more fully described in PCT Patent Application WO 94/15599 and other literature references. For example, taxanes having a C(10) keto substituent can be prepared by oxidation of 10-desacetyl taxanes. Taxanes which are dihydro substituted at C(10) can be prepared by reacting a C(10) hydroxy or acyloxy substituted taxane with samarium diiodide.

Taxanes having a C(14) substituent other than hydrogen may also be prepared. The starting material for these compounds may be, for example, a hydroxylated taxane (14-hydroxy-10-deacetylbaccatin III) which has been discovered in an extract of yew needles (C&EN, p 36–37, Apr. 12, 1993). Derivatives of this hydroxylated taxane having the various C(2), C(4), C(7), C(9), C(10), C3' and C5' functional groups described above may also be prepared by using this hydroxylated taxane. In addition, the C(14) hydroxy group together with the C(1) hydroxy group of 10-DAB can be converted to a 1,2-carbonate as described in C&EN or it may be converted to a variety of esters or other functional groups as otherwise described herein in connection with the C(2), C(4), C(9) and C(10) substituents.

The process of the present invention thus enables the preparation of taxanes having the following structure:

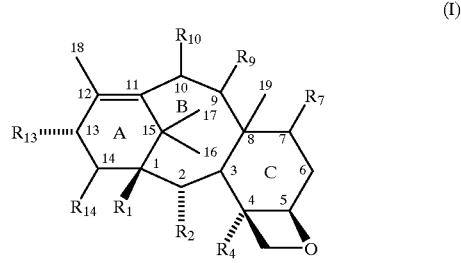

(I)

wherein

M comprises ammonium or is a metal;

$R_1$ is hydrogen, hydroxy, protected hydroxy, or together with $R_{14}$ or $R_2$ forms a carbonate;

$R_2$ is keto, —$OT_2$, acyloxy, or together with $R_1$ forms a carbonate;

$R_4$ is —$OT_4$ or acyloxy;

$R_7$ is hydrogen, halogen, —$OT_7$, or acyloxy;

$R_9$ is hydrogen, keto, —$OT_9$, or acyloxy;

$R_{10}$ is hydrogen, keto, —$OT_{10}$, or acyloxy;

$R_7$, $R_9$, and $R_{10}$ independently have the alpha or beta stereochemical configuration;

$R_{13}$ is hydroxy, protected hydroxy, keto, MO— or

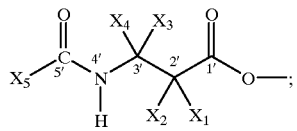

$R_{14}$ is hydrogen, —$OT_{141}$ acyloxy, or together with $R_1$, forms a carbonate;

$T_2$, $T_4$, $T_7$, $T_9$, $T_{10}$ and $T_{14}$ are independently hydrogen or hydroxy protecting group;

$X_1$ is —$OX_6$, —$SX_7$, or —$NX_8X_9$;

$X_2$ is hydrogen, hydrocarbyl, substituted hydrocarbyl, or heteroaryl;

$X_3$ and $X_4$ are independently hydrogen, hydrocarbyl, substituted hydrocarbyl, or heteroaryl;

$X_5$ is —$X_{10}$, —$OX_{10}$, —$SX_{10}$, —$NX_8X_{10}$, or —$SO_2X_{11}$;

$X_6$ is hydrogen, hydrocarbyl, substituted hydrocarbyl, heteroaryl, hydroxy protecting group, or a functional group which increases the water solubility of the taxane derivative;

$X_7$ is hydrocarbyl, substituted hydrocarbyl, heteroaryl, or sulfhydryl protecting group;

$X_8$ is hydrogen, hydrocarbyl, or substituted hydrocarbyl;

$X_9$ is an amino protecting group;

$X_{10}$ is hydrocarbyl, substituted hydrocarbyl, or heteroaryl;

$X_{11}$ is hydrocarbyl, substituted hydrocarbyl, heteroaryl, —$OX_{10}$, or —$NX_8X_{14}$;

$X_{14}$ is hydrogen, hydrocarbyl, substituted hydrocarbyl, or heteroaryl.

In one embodiment of the present invention, the substituents of the taxane (other than the C(7), C(10) and C(13) substituents) correspond to the substituents present on baccatin III or 10-DAB. That is, $R_{14}$ is hydrogen, $R_9$ is keto, $R_4$ is acetoxy, $R_2$ is benzoyloxy, and $R_1$ is hydroxy. In other embodiments, the taxane has a structure which differs from that of taxol or Taxotere® with respect to the C(13) side chain and at least one other substituent. For example, $R_{14}$ may be hydroxy; $R_2$ may be hydroxy, —$OCOZ_2$ or —$OCOOZ_{22}$ wherein $Z_2$ is hydrogen, hydrocarbyl, substituted hydrocarbyl, or heteroaryl and $Z_{22}$ is hydrocarbyl, substituted hydrocarbyl, or heteroaryl; $R_4$ may be hydroxy, —$OCOZ_4$ or —$OCOOZ_{44}$ wherein $Z_4$ is hydrogen, hydrocarbyl, substituted hydrocarbyl, or heteroaryl and $Z_{44}$ is hydrocarbyl, substituted hydrocarbyl, or heteroaryl; $R_7$ may be hydrogen, hydroxy, —$OCOZ_7$ or —$OCOOZ_{77}$ wherein $Z_7$ is hydrogen, hydrocarbyl, substituted hydrocarbyl, or heteroaryl and $Z_{77}$ is hydrogen, hydrocarbyl, substituted hydrocarbyl, or heteroaryl; $R_9$ may be hydrogen, hydroxy, —$OCOZ_9$ or —$OCOOZ_{99}$ wherein $Z_9$ is hydrogen, hydrocarbyl, substituted hydrocarbyl, or heteroaryl and $Zg_9$ is hydrogen, hydrocarbyl, substituted hydrocarbyl, or heteroaryl, and $R_{10}$ may be hydrogen, hydroxy, —$OCOZ_{10}$ or —$OCOOZ_{1010}$ wherein $Z_{10}$ is hydrogen, hydrocarbyl, substituted hydrocarbyl, or heteroaryl and $Z_{1010}$ is hydrogen, hydrocarbyl, substituted hydrocarbyl, or heteroaryl.

In a preferred embodiment, the taxane has the formula

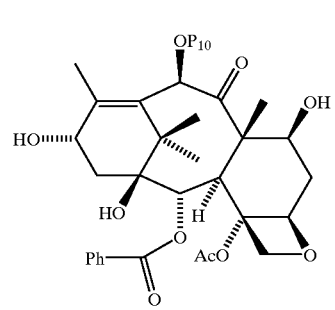

(IA)

wherein P10 is acyl, said acyl comprising at least three carbon atoms or two carbon atoms and a nitrogen, oxygen or sulfur atom. Stated another way, —$OP_{10}$ is other than acetoxy. More preferably, $P_{10}$ is —(C=O)$R_A$, —(C=O)$OR_B$, or —(C=O)$NR^C$ wherein $R_A$ is substituted or unsubstituted hydrocarbyl or heteroaryl, said unsubstituted hydrocarbyl comprising at least two carbon atoms; $R_B$ and $R_C$ are independently substituted or unsubstituted hydrocarbyl. Still more preferably, $R_A$ is substituted or unsubstituted alkyl or aryl, said unsubstituted alkyl comprising at least two carbon atoms; and $R_B$ and $R_C$ are independently substituted or unsubstituted alkyl or aryl.

In another embodiment of the invention, the taxane has the formula

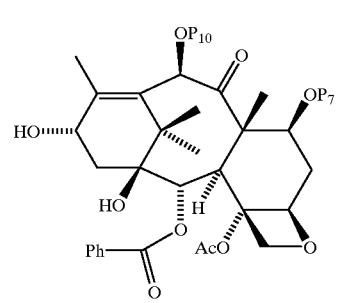

(II)

wherein $P_7$ and $P_{10}$ are independently substituted or unsubstituted acyl. In this embodiment, $P_7$ and P10 are preferably different.

Definitions

As used herein, the terms "selective" and "selective derivatization" shall mean that the desired product is preferentially formed over any other by-product. Preferably, the desired product is present in a molar ratio of at least 9:1 relative to any other by-product and, more preferably, is present in a molar ratio of at least 20:1 relative to any other by-product. In addition, "Ph" means phenyl; "Bz" means benzoyl; "Bn" means benzyl; "Me" means methyl; "Et" means ethyl; "iPr" means isopropyl; "tBu" and "t-Bu" means tert-butyl; "Ac" means acetyl; "TES" means triethylsilyl; "TMS" means trimethylsilyl; "TBS" means $Me_2t$-BuSi-; "CDI" means carbonyl diimidazole; "BOM" means benzyloxymethyl; "DBU" means diazabicycloundecane; "DMAP" means p-dimethylamino pyridine; "LHMDS" or "LiHMDS" means lithium hexamethyldisilazide; "DMF" means dimethylformamide; "10-DAB" means 10-desacetylbaccatin III; "Cbz" means benzyloxycarbonyl; "Alloc" means allyloxycarbonyl; "THF" means tetrahydrofuran; "BOC" means benzyloxycarbonyl; "PNB" means para-nitrobenzyl; "Troc" means 2,2,2- trichloroethoxycarbonyl; "EtOAc" means ethyl acetate; "THF" means tetrahydrofuran; "protected hydroxyl" means —OP wherein P is a hydroxyl protecting group; and "hydroxyl protecting group" includes, but is not limited to, acetals having two to ten carbons, ketals having two to ten carbons, and ethers, such as methyl, t-butyl, benzyl, p-methoxybenzyl, p-nitrobenzyl, allyl, trityl, methoxymethyl, methoxyethoxymethyl, ethoxyethyl, methoxy propyl, tetrahydropyranyl, tetrahydrothiopyranyl; and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloroethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl protecting groups may be found in "Protective Groups in Organic Synthesis" by T. W. Greene, John Wiley and Sons, 1981, and Second Edition, 1991.

The "hydrocarbon" and "hydrocarbyl" moieties described herein are organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbyl groups, and include alkaryl, alkenaryl and alkynaryl. Preferably, these moieties comprise 1 to 20 carbon atoms.

The alkyl groups described herein are preferably lower alkyl containing from one to six carbon atoms in the principal chain and up to 20 carbon atoms. They may be straight, branched chain or cyclic and include methyl, ethyl, propyl, isopropyl, butyl, hexyl and the like. They may be substituted with aliphatic or cyclic hydrocarbyl radicals.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like. They may be substituted with aliphatic or cyclic hydrocarbyl radicals.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like. They may be substituted with aliphatic or cyclic hydrocarbyl radicals.

The aryl moieties described herein contain from 6 to 20 carbon atoms and include phenyl. They may be hydrocarbyl substituted with the various substituents defined herein. Phenyl is the more preferred aryl.

The heteroaryl moieties described are heterocyclic compounds or radicals which are analogous to aromatic compounds or radicals and which contain a total of 5 to 20 atoms, usually 5 or 6 ring atoms, and at least one atom other than carbon, such as furyl, thienyl, pyridyl and the like. The heteroaryl moieties may be substituted with hydrocarbyl, heterosubstituted hydrocarbyl or hetero-atom containing substituents with the hetero-atoms being selected from the group consisting of nitrogen, oxygen, silicon, phosphorous, boron, sulfur, and halogens. These substituents include hydroxy; lower alkoxy such as methoxy, ethoxy, butoxy; halogen such as chloro or fluoro; ethers; acetals; ketals; esters; heteroaryl such as furyl or thienyl; alkanoxy; acyl; acyloxy; nitro; amino; and amido.

The substituted hydrocarbyl moieties described herein are hydrocarbyl moieties which are substituted with at least one atom other than carbon and hydrogen, including moieties in which a carbon chain atom is substituted with a hetero atom such as nitrogen, oxygen, silicon, phosphorous, boron, sulfur, or a halogen atom. These substituents include hydroxy; lower alkoxy such as methoxy, ethoxy, butoxy; halogen such as chloro or fluoro; ethers; acetals; ketals; esters; heteroaryl such as furyl or thienyl; alkanoxy; acyl; acyloxy; nitro; amino; and amido.

The acyl moieties and the acyloxy moieties described herein contain hydrocarbyl, substituted hydrocarbyl or heteroaryl moieties. In general, they have the formulas —C(O)G and —OC(O)G, respectively, wherein G is substituted or unsubstituted hydrocarbyl, hydrocarbyloxy, hydrocarbylamino, hydrocarbylthio or heteroaryl.

The ketal moieties described herein have the general formula

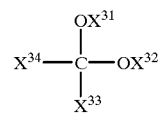

wherein $X^{31}$, $X^{32}$, $X^{33}$ and $X^{34}$ are independently hydrocarbyl, substituted hydrocarbyl or heteroaryl moieties. They may be optionally substituted with the various substituents defined herein. The ketal moieties are preferably substituted or unsubstituted alkyl or alkenyl, and more preferably substituted or unsubstituted lower ($C_1$–$C_6$) alkyl. These ketal moieties additionally may encompass sugars or substituted sugars and include ketal moieties prepared from sugars or substituted sugars such as glucose and xylose. When a ketal moiety is incorporated into a taxane of the present invention as a C(7) hydroxy protecting group, then either $X^{31}$ or $X^{32}$ represents the taxane moiety.

The acetal moieties described herein have the general formula

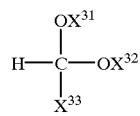

wherein $X^{31}$, $X^{32}$ and $X^{33}$ are independently hydrocarbyl, substituted hydrocarbyl or heteroaryl moieties. They may be optionally substituted with the various substituents defined herein other than hydroxyl. The acetal moieties are preferably substituted or unsubstituted alkyl or alkenyl, and more preferably substituted or unsubstituted lower ($C_1$–$C_6$) alkyl. These acetal moieties additionally may encompass sugars or substituted sugars and include acetal moieties prepared from sugars or substituted sugars such as glucose and xylose. When an acetal moiety is incorporated into a taxane of the present invention as a C(7) hydroxy protecting group, then either $X^{31}$ or $X^{32}$ represents the taxane moiety.

The term "taxane" as used herein, denotes compounds containing the A, B and C rings (with numbering of the ring positions shown herein):

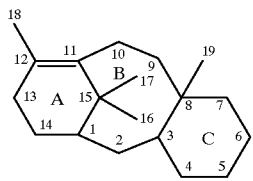

The following examples illustrate the invention.

EXAMPLE 1

A. Selective Acylation of a C(10) Hydroxyl Group

10-Cbz-10-DAB. To a solution of 10-DAB (30 mg, 0.055 mmol) in THF (1 mL) at room temperature was added dibenzyl pyrocarbonate (320 mg, 1.1 mmol, 20 equiv) under $N_2$. The reaction mixture was stirred at room temperature for 24 h. EtOAc (10 mL) was added, and the solution was quickly filtered through a short column of silica gel. The silica gel was washed with EtOAc (100 mL), and the solution was concentrated under reduced pressure. The residue was purified by flash column chromatography using EtOAc: hexanes (1:1) as the eluent and dried in vacuo overnight to give 10-cbz-10-DAB as a colorless solid: yield, 37 mg (98%). mp 205–206° C.; $[\alpha]_{Hg}$ −63° ($CHCl_3$, c=0.41); $^1H$ NMR (400 MHz, $CDCl_3$) δ 1.11(s, 3 H, Me17), 1.13(s, 3 H, Me16), 1.58(s, 1 H, 1-OH), 1.71(s, 3 H, Me19), 1.89(ddd, J=14.7, 10.9, 2.3 Hz, 1 H, H6b), 2.00(d, J=5.1 Hz, 1 H, 13-OH), 2.08(d, J=1.0, 3 H, Me18), 2.28(s, 3 H, 4-Ac), 2.30(m, 2 H, H14a, H14b), 2.43(d, J=4.1 Hz, 1 H, 7-OH), 2.58(ddd, J=14.7, 9.6, 6.6 Hz, 1 H, H6a), 3.88(d, J=6.9 Hz, 1 H, H3), 4.19(d, J=8.6 Hz, 1 H, H20b), 4.31(d, J=8.6 Hz, 1 H, H20a), 4.44(ddd, J=10.9, 6.6, 4.1 Hz, 1 H, H7), 4.89(m, 1 H, H13), 4.98(dd, J=9.6, 2.3 Hz, 1 H, H5), 5.23(d, J=12.1, 1 H, CHH'OC(O)), 5.26(d, J=12.1, 1 H, CHH'OC(O)), 5.65(d, J=6.9 Hz, 1 H, H2), 6.19(s, 1 H, H10), 7.35–7.44(m, 5 H, $PhCH_2O$), 7.48(dd, J=8.1, 7.6 Hz, 2 H, benzoate, m), 7.60(tt, J=7.6, 1.0 Hz, 1 H, benzoate, p), 8.11(d, J=8.1, 1.0 Hz, 2 H, benzoate, o) ppm. $^{13}C$ NMR (75 MHz, $CDCl_3$) δ 9.1(Me(19)), 15.3(Me(18)), 20.7(4-Ac), 22.3, 26.7(Me16, Me17), 35.5(C(6)), 38.6(C(14)), 42.5(C(15)), 46.1(C(3)), 58.7(C(8)), 67.9(C(13)), 70.5($OCH_2Ph$), 72.2, 75.0, 76.5(C(7), C(2), C(20)), 79.0, 79.1 (C(1), C(10)), 80.9(C(4)), 84.5(C(5)), 128.6, 128.8, 129.7, 130.3, 131.9, 133.8 ($OCH_2Ph$, benzoate), 135.1(C(11)), 147.5(C(12)), 155.6 (OC(O)O), 167.4(benzoate), 171.0(4-Ac), 204.7(C(9))ppm. Anal. Calcd for $C_{37}H_{42}O_{12}$. ½$H_2O$: C, 64.62; H, 6.30. Found: C, 64.34; H, 6.31.

10-Alloc-10-DAB. To a solution of 10-DAB (30 mg, 0.055 mmol) in THF (1 mL) at room temperature was added diallyl pyrocarbonate (366 mL, 2.2 mmol, 40 equiv) under $N_2$. The reaction mixture was stirred at room temperature for 48 h. TLC analysis indicated the presence of the desired product along with unreacted staring material. EtOAc (20 mL) was added, and the solution was quickly filtered through a short column of silica gel. The silica gel was washed with EtOAc (100 mL), and the solution was concentrated. The residue was purified by flash column chromatography using EtOAc: hexanes (1:1) as the eluent and dried in vacuo to overnight to give 10-alloc-10-DAB as a colorless solid: yield, 23 mg (67%, 95% at the conversion of 70%). The recovered 10-DAB, 9 mg (30%). 10-alloc-10-DAB: mp 201–203° C.; $[\alpha]_{Hg}$ −81° ($CHCl_3$, c=0.53); $^1H$ NMR (400 MHz, $CDCl_3$) δ 1.11 (s, 3 H, Me17) 1.12(s, 3 H, Me16), 1.60(s, 1 H, 1-OH), 1.69(s, 3 H, Me19), 1.87(ddd, J=14.7, 11.0, 2.1 Hz, 1 H, H6b), 2.05(d, J=5.1 Hz, 1 H, 13-OH), 2.08(d, J=1.2, 3 H, Me18), 2.28(s, 3 H, 4-Ac), 2.29(m, 2 H, H14a, H14b), 2.47(d, J=4.2 Hz, 1 H, 7-OH), 2.57(ddd, J=14.7, 9.6, 6.7 Hz, 1 H, H6a), 3.86(d, J=7.0 Hz, 1 H, H3), 4.16(d, J=8.4 Hz, 1 H, H20b), 4.31(d, J=8.4 Hz, 1 H, H20a), 4.44(ddd, J=11.0, 6.7, 4.2 Hz, 1 H, H7), 4.70(br d, J=5.9 Hz, 2 H, $CHH'=CHCH_2O$), 4.90(m, 1 H, H13), 4.97(dd, J=9.6, 2.1 Hz, 1 H, H5), 5.32(dd, J=10.4, 1.2 Hz, 1 H, $CHH'=CHCH_2O$), 5.42(dd, J=17.2, 1.2 Hz, 1 H, $CHH'=CHCH_2O$), 5.63(d, J=7.0 Hz, 1 H, H2), 5.98(ddt, J=17.2, 10.4, 5.9 Hz, 1 H, $CHH'=CHCH_2O$), 6.16(s, 1 H, H10), 7.48(dd, J=8.1, 7.5 Hz, 2 H, benzoate, m), 7.60(tt, J=7.5, 1.2 Hz, 1 H, benzoate, p), 8.11(d, J=8.1, 1.2 Hz, 2 H, benzoate, o) ppm; $^{13}C$ NMR (75 MHz, $CDCl_3$) α 9.1(Me(19)), 15.3 (Me(18)), 20.7(4-Ac), 22.3, 26.7(Me16, Me17), 35.5(C(6)), 38.6(C(14)), 42.5(C(15)), 46.1(C(3)), 58.7(C(8)), 67.9(C(13)), 69.3( $CH_2=CHCH_2O$), 72.1, 75.0, 76.5(C(7), C(2), C(20)), 79.0, 79.1(C(1), C(10)), 80.9(C(4)), 84.5(C(5)), 119.6($CH_2=CHCH_2O$), 128.8, 129.7, 130.3, 133.8 (benzoate), 131.4, 13 1. 9($CH_2=CHCH_2O$, C(11)) 147.5(C(12)), 155.4(OC(O)O), 167.4(benzoate), 170. 9(4-Ac), 204.7(C (9) )ppm. Anal. Calcd for $C_{33}H_{40}O_{12}$: C, 63.05; H, 6.41. Found: C, 62.77; H, 6.48.

B. Selective Acylation of a C(10) Hydroxyl Group Using $ZnCl_2$ baccatin III. To a solution of 10-DAB (100 mg, 0.184 mmol) in THF (6 mL) at room temperature was added a mixture of acetic anhydride (6.5 mL) and $ZnCl_2$/THF solution (0.5 M, 726 mL, 0.368 mmol, 2 equiv) under $N_2$. The reaction mixture was stirred at room temperature for 4 h. Then the reaction mixture was diluted with EtOAc (100 mL), washed with saturated aqueous NaHCO3 solution (40 mLx3), brine. The organic layer was dried over $Na_2SO_4$, concentrated under reduced pressure. The residue was purified by flash column chromatography using EtOAc: hexanes (1:1) as the eluent and dried in vacuo to give baccatin III as a colorless solid: yield, 100 mg (93%). mp 237–238° C. dec (ref 236–238° C. dec); $[\alpha]_{Hg}$ −63° ($CH_3OH$, c=0.45) (ref $[\alpha]_D$ −54°, $CH_3OH$); $^1H$ NMR (400 MHz, $CDCl_3$) α 1.1l(s, 6 H, Me16, Me17), 1.61(s, 1 H, 1-OH), 1.67(s, 3 H, Me19), 1.87(ddd, J=14.7, 10.9, 2.1 Hz, 1 H, H6b), 2.05(d, J=3.8 Hz, 1 H, 13-OH), 2.05(s, 3 H, Me18), 2.24(s, 3 H, 10-Ac), 2.28(s, 3 H, 4-Ac), 2.30(m, 2 H, H14a, H14b), 2.47(d, J=4.2 Hz, 1 H, 7-OH), 2.57(ddd, J=14.7, 9.4, 6.7 Hz, 1 H, H6a), 3.89(d, J=7.0 Hz, 1 H, H3), 4.16(d, J=8.4 Hz, 1 H, H20b), 4.31(d, J=8.4 Hz, 1 H, H20a), 4.47(ddd, J=10.9, 6.7, 4.2 Hz, 1 H, H7), 4.90(m, 1 H, H13), 4.99(dd, J=9.4, 2.1 Hz, 1 H, H5), 5.63(d, J=7.0 Hz, 1 H, H2), 6.33(s, 1 H, H10), 7.48(dd, J=7.8, 7.8 Hz, 2 H, benzoate, m), 7.61(dd, J=7.8, 7.4 Hz, 1 H, benzoate, p), 8.11(d, J=7.4 Hz, 2 H, benzoate, o)ppm. $^{13}C$ NMR (100 MHz, $CDCl_3$) α 9.4(Me(19)), 15.6(Me(18)), 20.9(4-Ac, 10-Ac), 22.6, 27.0(Me16, Me17), 35.6(C(6)), 38.6(C(14)), 42.7(C(15)), 46.1(C(3)), 58.8(C(8)), 68.0(C(13)), 72.3, 75.0, 76.2, 76.4(C(7), C(2), C(10), C(20)), 79.1(C(1)), 80.9(C(4)), 84.5(C(5)), 128.6, 129.4, 130.1, 133.7(benzoate), 132.0(C(11)), 146.3(C(12)), 167.1 (benzoate), 170.7, 171.3(10-Ac, 4-Ac), 204.1(C(9))ppm.

10-Chloroacetyl-10-DAB. To a solution of 10-DAB (116 mg, 0.21 mmol) in THF (3 mL) at room temperature was added a mixture of chloroacetic anhydride (2.8 g, 16.3 mmol, 78 equiv) and $ZnCl_2$/THF solution (0.5 M, 0.85 mL, 0.42 mmol, 2 equiv) via a syringe under $N_2$. The reaction mixture was stirred at room temperature for 5 h. The reaction mixture was poured into a mixture of EtOAc (200 mL) and saturated aqueous $NaHCO_3$ solution (100 mL). The organic layer was separated, and the aqueous layer was extracted with EtOAc (100 mLx3). The organic solution was combined, dried over $Na_2SO_4$, filtered, and concentrated under reduced pressure. The residue was purified by flash column chromatography using EtOAc: hexanes (1:1) as the eluent and dried overnight in vacuo to give 10-chloro-acetyl-10-DAB as a colorless solid: yield, 123 mg (93%). mp 231–233° C. dec; $[\alpha]_{Hg}$ −66° (EtOAc, c=0.45); $^1$H NMR (400 MHz, $CDCl_3$) δ 1.11(s, 3 H, Me17), 1.12(s, 3 H, Me16), 1.63(s, 1 H, 1-OH), 1.69(s, 3 H, Me19), 1.89(ddd, J=14.6, 10.9, 2.1 Hz, 1 H, H6b), 2.07(d, J=5.2 Hz, 1 H, 13-OH), 2.09(d, J=1.2, 3 H, Me18), 2.12(d, J=4.5 Hz, 1 H, 7-OH), 2.29(s, 3 H, 4-Ac), 2.30(m, 2 H, H14a, H14b), 2.58(ddd, J=14.6, 9.7, 6.7 Hz, 1 H, H6a), 3.88(d, J=7.0 Hz, 1 H, H3), 4.16(d, J=8.3 Hz, 1 H, H20b), 4.27(br s, 2 H, $ClCH_2$), 4.31(d, J=8.3 Hz, 1 H, H20a), 4.44(ddd, J=10.9, 6.7, 4.5 Hz, 1 H, H7), 4.90(m, 1 H, H13), 4.98(dd, J=9.7, 2.1 Hz, 1 H, H5), 5.64(d, J=7.0 Hz, 1 H, H2), 6.41(s, 1 H, H10), 7.49(dd, J=7.9, 7.4 Hz, 2 H, benzoate, m), 7.61(tt, J=7.4, 1.3 Hz, 1 H, benzoate, p), 8.11(d, J=7.9, 1.3 Hz, 2 H, benzoate, o) ppm. $^{13}$C NMR (75 MHz, $CDCl_3$) Y9.3(Me(19)), 15.3 (Me(18)), 20.6(4-Ac), 22.3, 26.7(Me16, Me17), 35.8(C(6)), 38.6(C(14)), 40.5($ClCH_2$), 42.6(C(15)), 46.2(C(3)), 58.8(C(8)), 68.0(C(13)), 72.0, 75.0, 75.9(C(7), C(2), C(10), C(20)), 79.0(C(1)), 80.9(C(4)), 84.4(C(5)), 128.8, 129.7, 130.3, 133.9(benzoate), 131.8(C(11)), 147.1(C(12)), 167.4, 167.7 ($ClCH_2C(O)O$, benzoate), 171.0(4-Ac), 203.7(C(9))ppm. Anal. Calcd for $C_{31}H_{37}C_{11}$. $H_2O$: C, 58.26; H, 6.15. Found: C, 58.26; H, 6.07.

10-Propionyl-10-DAB. To a solution of 10-DAB (47 mg, 0.086 mmol) in THF (2 mL) at room temperature was added a mixture of propionic anhydride anhydride (4 mL) and $ZnCl_2$/THF solution (0.5 M, 350 mL, 0.173 mmol, 2 equiv) under $N_2$. The reaction mixture was stirred at room temperature for 14 h. Then the reaction mixture was diluted with EtOAc (150 mL), exhaustively washed with saturated aqueous $NaHCO_3$ solution (50 mLx3), brine. The organic layer was dried over $Na_2SO_4$, concentrated under reduced pressure. The residue was purified by flash column chromatography using EtOAc: hexanes (1:1) as the eluent and dried in vacuo to give 10-propionyl-10-DAB as a white solid: yield, 48 mg (93%). mp 212–213° C. dec; $[\alpha]_{Hg}$ −96° ($CHCl_3$, c=0.78);$^1$H NMR (400 MHz, $CDCl_3$) δ 1.11(s, 6 H, Me16, Me17), 1.24(t, J=7.6 Hz, 3 H, $CH_3CH_2$), 1.60(s, 1 H, 1-OH), 1.67(s, 3 H, Me19), 1.87(ddd, J=14.7, 10.9, 2.2 Hz, 1 H, H6b), 2.05(d, J=5.1 Hz, 1 H, 13-OH), 2.06(d, J=1.3 Hz, 3 H, Me18), 2.28(s, 3 H, 4-Ac), 2.30(d, J=7.5 Hz, 2 H, H14a, H14b), 2.51(d, J=4.1 Hz, 1 H, 7-OH), 2.55(q, J=7.6 Hz, 2 H, $CH_3CH_2$), 2.57(ddd, J=14.7, 9.5, 6.7 Hz, 1 H, H6a), 3.90(d, J=6.9 Hz, 1 H, H3), 4.16(dd, J=8.4, 0.8 Hz, 1 H, H20b), 4.31(d, J=8.4 Hz, 1 H, H20a), 4.48(ddd, J=10.9, 6.7, 4.1 Hz, 1 H, H7), 4.90(m, 1 H, H13), 4.99(dd, J=9.5, 2.2 Hz, 1 H, H5), 5.63(d, J=6.9 Hz, 1 H, H2), 6.34(s, 1H, H10), 7.48(dd, J=8.1, 7.4 Hz, 2 H, benzoate, m), 7.61(tt, J=7.4, 1.3 Hz, 1 H, benzoate, p), 8.11(dd, J=8.3, 1.3 Hz, 2 H, benzoate, o) ppm. ° C. NMR (75 MHz, $CDCl_3$) δ 8.8($CH_3CH_2$), 9.2(Me(19)), 15.2(Me(18)), 20.7(4-Ac), 22.3, 26.8, 27.4(Me16, Me17, $CH_3CH_2$), 35.5(C(6)), 38.7(C(14)), 42.6(C(15)), 46.1(C(3)), 58.7(C(8)), 67.9(C(13)), 72.3, 75.1, 76.1, 76.5(C(7), C(2), C(10), C(20)), 79.1(C(1)), 80.9(C(4)), 84.5(C(5)), 128.7, 129.7, 130.3, 133.8(benzoate), 132.3(C(11)), 146.5(C(12)), 167.4(benzoate), 170.9, 174.9(4-Ac, 10-C(O)O), 204.6(C(9))ppm. Anal. Calcd for $C_{32}H_{40}O_{11}$: C, 63.99; H, 6.71. Found: C, 63.81; H, 6.80.

C. Selective Acylation of a C(10) Hydroxyl Group Using $CeCl_3$

General procedure: To a solution of 10-DAB in THF (20 mL per mmol of 10-DAB) under $N_2$ was added $CeCl_3$ and the appropriate anhydride or pyrocarbonate (amounts specified in Table 1). The reaction mixture was stirred at 25° C. and monitored by TLC analysis. When that analysis indicated complete reaction (time specified in Table 1), the reaction mixture was diluted with EtOAc and washed three times with saturated aqueous sodium bicarbonate solution. The combined bicarbonate washings were extracted three times with EtOAc, the organic layers were combined and dried over sodium sulfate, and the solvent was evaporated. The crude product was purified by flash column chromatography. Further purification, if necessary, was carried out by recrystallization from EtoAc/Hexane.

TABLE 1

$CeCl_3$ catalyzed acylation of 10-DAB $$10\text{-DAB} \xrightarrow[\text{THF, RT}]{(RCO)_2O,\ CeCl_3} 10\text{-Acyl-10-DAB}$$

| Entry | R (eq) | $CeCl_3$ (eq) | Time (hr) | Yield (%) |
|---|---|---|---|---|
| 1 | Me (10) | 0.1 | 1.5 | 91 |
| 2 | Pr (10) | 0.1 | 3 | 100 |
| 3 | iPr (10) | 0.1 | 4.5 | 100 |
| 4 | Ph (10) | 0.1 | 21 | 94 |
| 5 | cyclopropyl (10) | 0.1 | 20.5 | 94 |
| 6 | MeCH═CH (10) | 0.1 | 20 | 91 |
| 7 | $CH_2$═$CHCH_2O$ (5) | 0.1 | 1 | 96 |
| 8 | EtO (5) | 0.1 | 3 | 99 |
| 9 | MeO (5) | 0.1 | 3 | 98 |
| 10 | tBuO (10) | 0.7 | 24 | 94 |
| 11 | BnO (3) | 0.7 | 1 | 98 |

10butyryl-10-DAB. mp 145–149° C.; $[\alpha]_{Hg}$ −86.6° ($CHCl_3$, c=1); $^1$H NMR (500 MHz, $CDCl_3$) δ 8.13–8.11 (2H, m), 7.62 (1H, m), 7.51–7.48 (2H, m), 6.35 (1H, s), 5.64 (1H, d, J 7.0 Hz), 4.99 (1H, d, J 7.7 Hz), 4.90 (1H, m)), 4.48 (1H, m), 4.31 (1H, d, J 8.3 Hz), 4.18 (1H, d, J 8.3 Hz), 3.91 (1H, d, J 7.0 Hz), 2.60–2.42 (4H, m), 2.36–2.26 (2H, m), 2.28 (3H, s), 2.06 (3H, d, J 1.0 Hz), 1.88 (1H, ddd, J 1.9, 10.9, 13.0 Hz), 1.76 (2H, hex, J 7.4 Hz), 1.68 (3H, s), 1.12 (6H, s) and 1.04 (3H, t, J 7.4 Hz); $^{13}$C NMR (100 MHz, $CDCl_3$) δ 204.2, 173.9, 170.6, 167.1, 146.2, 133.7, 132.0, 130.1, 129.4, 128.6, 84.5, 79.1, 76.5, 76.0, 75.0, 72.3, 68.0, 58.8, 46.2, 38.7, 37.1, 36.2, 35.6, 30.6, 27.0, 22.6, 20.9, 18.4, 17.8, 15.5 and 9.4; Anal. Calcd. for $C_{33}H_{42}O_{11}$: C, 64.48; H, 6.89 Found: C, 63.67; H, 7.01.

10-isobutyryl-10-DAB. mp 143° C.; $[\alpha]_{Hg}$ −62.6° ($CHCl_3$, c=0.075); $^1$H NMR ($CDCl_{31}$ 500 MHz): δ 8.12 (2H, d, J 7.3 Hz), 7.62 (1H, m), 7.51–7.48 (2H, m), 6.33 (1H, s), 5.65 (1H, d, J 7.3 Hz), 5.00 (1H, d, J 7.9 Hz), 4.91 (1H, m), 4.48 (1 H ddd, J 4.3, 6.7, 11.0 Hz), 4.31 (1H, d, J 8.6 Hz), 4.18 (1H, d, J 8.6 Hz), 3.91 (1H, d, J 7.3 Hz), 2.74 (1H, pent, J 6.7 Hz), 2.57 (1H, m), 2.51 (1H, d, J 4.3 Hz), 2.31 (1H, m), 2.28 (3H, s), 2.06 (3H, s), 2.01 (1H, d, J 5.5 Hz), 1.90 (1H, ddd, J 2.3, 11.0, 14.6 Hz), 1.68 (3H, s), 1.60 (1H, s), 1.51 (3H, s), 1.33 (3H, d, J 6.7 Hz), 1.26 (3H, d, J 6.7 Hz), 1.13 (3H, s) and 1.12 (3H, s); $^{13}$C NMR (100 MHz, $CDCl_3$) δ 204.1, 177.2, 170.6, 167.1, 146.2, 133.7, 132.1, 130.1, 129.4, 128.6, 95.5, 84.5, 80.9, 79.1, 76.5, 75.8, 74.9, 72.3, 68.0, 58.8, 46.2, 42.7, 38.7, 35.6, 34.1, 27.0, 22.6, 20.9, 19.2, 18.7, 15.5 and 9.4; Anal. Calcd. for $C_{33}H_{42}O_{11}$.$0.5H_2O$: C, 64.48; H, 6.89 Found: C, 63.05; H, 6.70.

10-benzoyl-10-DAB. $^1$H NMR ($CDCl_3$, 500 MHz): δ 8.15–8.11 (4H, m), 7.64–7.6 (2H, m), 7.52–7.48 (4H, m), 6.62 (1H, s), 5.7 (1H, d, J 7.1 Hz), 5.02 (1H, d, J 7.7 Hz), 4.94 (1H, m), 4.57 (1H, ddd, J 4.4, 7.1, 11.0 Hz), 4.33 (1H, d, J 8.2 Hz), 4.20 (1H, d, J 8.3 Hz), 3.99 (1H, d, J 6.6 Hz), 2.62 (1H, ddd, J 6.6, 9.3, 14.8), 2.55 (1H, d, J 4.4 Hz), 2.35

(2H, m), 2.30 (3H, s), 2.13 (3H, d, J 1.1 Hz), 2.03 (1H, d, J 4.9 Hz), 1.91 (1H, ddd, J 2.2, 11.0, 13.2 Hz), 1.71 (3H, s), 1.65 (1H, s), 1.25 (3H, s) and 1.21 (3H, s); $^{13}$C NMR (100 MHz, CDCl$_3$) δ 204.0, 170.7, 167.1, 166.5, 146.5, 133.7, 133.6, 132.0, 130.1, 129.9, 129.4, 129.3, 128.7, 128.5, 84.5, 80.9, 79.1, 76.5, 75.0, 72.4, 68.1, 58.8, 46.3, 42.8, 38.7, 35.8, 29.7, 27.2, 22.6, 21.2, 15.6 and 9.5; Anal. Calcd. for C$_{35}$H$_{40}$O$_{11}$: C, 66.66; H, 6.22 Found C, 66.46; H, 6.19.

10-trans crotonyl-10-DAB. $^1$H NMR (CDCl$_3$, 500 MHz): δ 8.13 (2H, d, J 7.1 Hz), 7.62 (1H, m), 7.51–7.48 (2H, m), 7.11 (1H, m), 6.42 (1H, s), 6.02 (1H, dq, J 1.7, 15.4 Hz), 5.66 (1H, d, J 7.1 Hz), 4.99 (1H, dd, J 2.0, 9.6 Hz), 4.91 (1H, t, J 7.6 Hz), 4.50 (1H, dd, J 7.1., 10.8 Hz), 4.31 (1H, d, J 8.3 Hz), 4.19 (1H, d, J 8.3 Hz), 3.93 (1H, d, J 7.1 Hz), 2.61–2.55 (2H, m), 2.33–2.31 (2H, m), 2.28 (3H, s), 2.07 (3H, d, J 1.5 Hz), 1.95 (3H, dd, J 1.6, 6.8 Hz), 1.89 (1H, ddd, J 2.3, 11.0, 13.4 Hz), 1.68 (3H, s), 1.15 (3H, s) and 1.14 (3H, s); $^{13}$C NMR (75 MHz, CDCl$_3$) δ 212.4, 181.0, 170.8, 167.3, 166.5, 146.4, 133.8, 132.3, 130.2, 129.5, 128.7, 121.9, 116.0, 84.7, 84.6, 80.9, 79.2, 77.2, 75.9, 75.1, 72.4, 68.1, 58.8, 46.1, 42.7, 38.6, 35.6, 27.0, 20.9, 18.0, 15.4 and 9.3; Anal. Calcd. for C$_{33}$H$_{40}$O$_{11}$: C, 64.69; H, 6.58 Found C, 63.93; H, 6.61.

10-cyclopropanoyl-10-DAB. $^1$H (CDCl$_3$, 500 MHz): δ 8.12 (2H, d, J 7.3 Hz), 7.62 (1H, t, J 7.5 Hz), 7.49 (2H, t, J 7.7 Hz), 6.35 (1H, s), 5.65 (1H, d, J 7.0 Hz), 4.99 (1H, app-d, J 8.2 Hz), 4.91 (1H, m), 4.46 (1H, ddd, J 4.1, 6.8, 10.8 Hz), 4.31 (1H, d, J 8.1 Hz), 4.18 (1H, d, J 8.1 Hz), 3.90 (1H, d, J 7.0 Hz), 2.56 (1H, m), 2.51 (1H, d, J 4.1 Hz), 2.31 (2H, m), 2.07 (3H, d, J 1.0 Hz), 2.00 (1H, d, J 4.9 Hz), 1.87 (1H, ddd, J 2.1, 10.8, 14.6 Hz), 1.79 (1H, ddd, J 3.4, 7.9, 12.4 Hz), 1.68 (3H, s), 1.60 (1H, s), 1.16–1.14 (2H, m), 1.13 (6H, s) and 1.01–0.97 (2H, m); $^{13}$C NMR (100 MHz, CDCl$_3$) δ 204.3, 175.2, 170.6, 167.1, 146.4, 133.7, 132.0, 130.1, 129.4, 128.6, 84.5, 80.9, 79.1, 76.5, 76.0, 74.9, 72.4, 68.0, 58.8, 46.2, 42.7, 38.6, 35.6, 34.0, 27.0, 25.6, 24.9, 22.6, 21.0, 15.6, 13.1, 9.4 and 9.1; Anal. Calcd. for C$_{33}$H$_{40}$O$_{11}$: C, 64.69; H, 6.58 Found: C, 64.47; H, 6.66.

10-Ethoxycarbonyl-10-DAB. mp 214–215° C.; [α]$_{Hg}$ –81° (CHCl$_3$, c=0.35); $^1$H NMR (500 MHz, CDCl$_3$) δ 1.13(s, 3 H, Me17), 1.14(s, 3 H, Me16), 1.38(t, J=7.1 Hz, 3 H, CH$_3$CH$_2$), 1.59(s, 1 H, 1-OH), 1.70(s, 3 H, Me19), 1.88(ddd, J=14.6, 10.5, 2.1 Hz, 1 H, H6b), 2.00(d, J=5.0 Hz, 1 H, 13-OH), 2.10(d, J=1.4 Hz, 3 H, Me18), 2.28(s, 3 H, 4-Ac), 2.30(m, 2 H, H14a, H14b), 2.46(d, J=4.2 Hz, 1 H, 7-OH), 2.57(ddd, J=14.6, 9.6, 6.7 Hz, 1 H, H6a), 3.88(d, J=6.9 Hz, 1 H, H3), 4.18(d, J=8.2 Hz, 1 H, H20b), 4.31(d, J=8.2 Hz, 1 H, H20a), 4.23–4.33(m, 2 H, CH$_3$CH$_2$), 4.44 (ddd, J=10.5, 6.7, 4.2 Hz, 1 H, H7), 4.90(m, 1 H, H13), 4.98(dd, J=9.6, 2.1 Hz, 1 H, H5), 5.65(d, J=6.9 Hz, 1 H, H2), 6.17(s, 1 H, H10), 7.48(dd, J=8.2, 7.3 Hz, 2 H, benzoate, m), 7.60(tt, J=7.3, 1.4 Hz, 1 H, benzoate, p), 8.11(d, J=8.2, 1.4 Hz, 2 H, benzoate, o) ppm; $^{13}$C NR (75 MHz, CDCl$_3$) δ 9.2, 14.0, 15.5, 20.8, 22.4, 26.7, 35.4, 38.5, 42.4, 46.0, 58.6, 65.0, 67.7, 72.2, 74.9, 76.4, 78.7, 79.0, 80.6, 84.4, 128.7, 129.4, 130.1, 131.5, 133.7, 147.5, 155.4, 167.1, 170.8, 204.7 ppm.

10-Methoxycarbonyl-10-DAB. mp 218–219° C.; [α]$_{Hg}$ –83° (CHCl$_3$, c=0.58); $^1$H NMR (500 MHz, CDCl$_3$) δ 1.12(s, 3 H, Me17), 1.13(s, 3 H, Me16), 1.59(s, 1 H, 1-OH), 1.70(s, 3 H, Me19), 1.88(ddd, J=14.7, 10.8, 1.8 Hz, 1 H, H6b), 2.00(d, J=5.0 Hz, 1 H, 13-OH), 2.10(d, J=1.4 Hz, 3 H, Me18), 2.28(s, 3 H, 4-Ac), 2.30(m, 2 H, H14a, H14b), 2.40(d, J=4.1 Hz, 1 H, 7-OH), 2.57(ddd, J=14.7, 9.7, 6.6 Hz, 1 H, H6a), 3.87(d, J=6.9 Hz, 1 H, H3), 3.88(s, 3 H, MeOC(O)), 4.18(d, J=8.4 Hz, 1 H, H20b), 4.31(d, J=8.4 Hz, 1 H, H20a), 4.44(ddd, J=10.8, 6.6, 4.1 Hz, 1 H, H7), 4.90(m, 1 H, H13), 4.98(dd, J=9.7, 1.8 Hz, 1 H, H5), 5.65(d, J=6.9 Hz, 1 H, H2), 6.17(s, 1 H, H10), 7.48(t, J=8.2, 7.3 Hz, 2 H, benzoate, m), 7.61(tt, J=7.3, 1.4 Hz, 1 H, benzoate, p), 8.11(d, J=8.2, 1.4 Hz, 2 H, benzoate, o) ppm; $^{13}$C NMR (75 MHz, CDCl$_3$) δ 9.2, 15.5, 20.7, 22.4, 26.7, 35.5, 38.5, 42.4, 46.0, 55.4, 58.6, 65.0, 67.7, 72.1, 74.8, 76.4, 78.9, 79.0, 80.6, 84.4, 128.7, 129.4, 130.1, 131.4, 133.7, 147.5, 155.9, 167.1, 170.8, 204.6 ppm.

10-tBoc-10-DAB. mp 193–194° C.; [α]$_{Hg}$ –820 (CHCl$_{31}$ c=0.33); $^1$H NMR (500 MHz, CDCl$_3$) δ 1.13(s, δ 1H, Me17, Me16), 1.48(s, 9 H, tBuO), 1.58(s, 1 H, 1-OH), 1.69(s, 3 H, Me19), 1.88(ddd, J=14.9, 11.0, 2.2 Hz, 1 H, H6b), 1.99(d, J=5.0 Hz, 1 H, 13-OH), 2.08(d, J=1.4 Hz, 3 H, Me18), 2.28(s, 3 H, 4-Ac), 2.30(m, 2 H, H14a, H14b), 2.56(ddd, J=14.9, 9.6, 6.9 Hz, 1 H, H6a), 2.68(d, J=3.6 Hz, 1 H, 7-OH), 3.88(d, J=6.9 Hz, 1 H, H3), 4.19(d, J=8.2 Hz, 1 H, H20b), 4.31(d, J=8.2 Hz, 1 H, H20a), 4.46(ddd, J=11.0, 6.9, 3.6 Hz, 1 H, H7), 4.90(m, 1 H, H13), 4.99(dd, J=9.6, 2.2 Hz, 1 H, H5), 5.64(d, J=6.9 Hz, 1 H, H2), 6.11(s, 1 H, H10), 7.48(t, J=7.8 Hz, 2 H, benzoate, m), 7.60(tt, J=7.8, 1.3 Hz, 1 H, benzoate, p), 8.11(dd, J=7.8, 1.3 Hz, 2 H, benzoate, o) ppm; $^{13}$C NMR (75 MHz, CDCl$_3$) δ 9.2, 15.6, 20.9, 22.4, 26.8, 27.5, 35.3, 38.5, 42.5, 45.9, 58.7, 67.9, 72.3, 74.7, 76.4, 78.0, 79.2, 80.8, 83.8, 84.5, 128.7, 129.4, 130.1, 131.8, 133.7, 147.3, 154.0, 167.2, 170.8, 205.0 ppm.

D. Selective Carbamoylation of a C(10) Hydroxyl Group

General procedure for the Selective Carbamoylation of the C-10 Hydroxyl group of 10-DAB: A solution of 0.061 mmol (1.1 mol equiv) of the isocyanate in 2 mL of THF was added, under nitrogen, to a mixture of 10-DAB (30 mg, 0.055 mmol) and CuCl (5.5 mg, 0.055 mmol) at 0° C. The mixture was stirred for the time indicated in Table 2. After this time the reaction was warmed to 25°C. and stirring was continued for the time indicated in Table 2. The reaction was quenched by the addition of saturated aqueous ammonium chloride solution, and the mixture was extracted three times with EtOAc. The combined organic layers were washed with saturated aqueous NaHCO$_3$ solution, dried over sodium sulfate, and the solvent was evaporated to yield a white solid. The product was purified by column chromatography using 2:1 EtOAc/hexane as the eluent.

TABLE 2

Carbamoylation of 10-DAB

10-DAB $\xrightarrow{\text{RNCO, CuCl, THF}}$ 10-Carbamoyl-10-DAB

| Entry | R (eq) | Temp (° C.) | Time (hr) | Yield (%) |
|---|---|---|---|---|
| 1 | Et (1.1) | 0 | 7.5 | 88 |
|   |   | rt | 0.5 |   |
| 2 | allyl (1.1) | 0 | 6 | 88 |
|   |   | rt | 0.5 |   |
| 3 | Bu (1.1) | 0 | 6.5 | 87 |
|   |   | rt | 0.5 |   |
| 4 | Ph (1.1) | rt | 3 | 94 |

10-ethylcarbamoyl-0-DAB. mp 241–243° C.; [α]$_{Hg}$ –92.0° (CHCl$_3$, c=0.5); $^1$H NMR (400 MHz, CDCl$_3$) δ 8.13 (2H, d, J 7.1 Hz), 7.63 (1H, m), 7.52–7.48 (2H, m), 6.27 (1H, s), 5.63 (1H, d, J 6.9 Hz), 5.01 (1H, dd, J 1.9, 9.6 Hz), 4.97 (1H, m), 4.91 (1H, m), 4.50 (1H, ddd, J 3.7, 6.5, 10.5 Hz), 4.31 (1H, d, J 8.3 Hz), 4.17 (1H, d, J 8.3 Hz), 3.88 (1H, d, J 7.0 Hz), 3.32–3.25 (2H, m), 3.10 (1H, d, J 3.7 Hz), 2.56 (1H, ddd, J 6.8, 9.8, 14.8 Hz), 2.31 (1H, m), 2.29 (3H, S), 2.09 (3H, S), 1.88 (1H, ddd, J 2.2, 11.0, 13.3 Hz), 1.67 (3H, s), 1.60 (1H, s), 1.19 (3H, t, J 7.2 Hz) and 1.10 (6H, s); Anal. Calcd. for $C_{32}H_{40}NO_{11}$: C, 62.43; H, 6.71 Found: C, 61.90; H, 6.77.

10-butylcarbamoyl-10-DAB. $[\alpha]_{Hg}$ −89.6° (CHCl$_3$, c=0.25); $^1$H NMR (500 MHz, CDCl$_3$) δ 8.12 (2H, d, J 7.3 Hz), 7.61 (1H, m), 7.51–7.45 (2H, m), 6.27 (1H, s), 5.64 (1H, d, J 6.7 Hz), 5.00 (1H, d, J 8.0 Hz), 4.91 (1H, m), 4.49 (1H, m), 4.31 (1H, d, J 8.5 Hz), 4.19 (1H, d, J 8.5 Hz), 3.89 (1H, d, J 6.7 Hz), 3.25–3.23 (2H, m), 3.04 (1H, m), 2.56 (1H, ddd, J 6.7, 9.7, 14.7 Hz), 2.30 (1H, d, J 7.9 Hz), 2.28 (3H. s), 2.09 (3H, s), 1.99 (1H, d, J 4.9 Hz), 1.88 (1H, ddd, J 2.5, 11.0, 13.4 Hz), 1.68 (3H, s), 1.59 (1H, s), 1.55 (2H, b), 1.42–1.37 (2H, m), 1.11 (6H, s) and 0.95 (3H, t, J 7.6 Hz); Anal. Calcd. for $C_{34}H_{44}NO_{11}$: C, 63.44; H, 7.05 Found: C, 62.64; H, 7.01.

10-phenylcarbamoyl-10-DAB. mp 178–180° C.; $[\alpha]_{Hg}$ −93.0° (CHCl$_3$, c=0.5); $^1$H NMR(400 Hz, CDCl$_3$) δ 8.13 (2H, d, J 6.9 Hz), 7.63 (1H, t, J 7.4 Hz), 7.51 (2H, t, J 7.6 Hz), 7.42 (1H, d, J 7.8 Hz), 7.36–7.32 (2H, m), 7.12 (1H, t, J 7.4 Hz), 6.87 (1H, b), 6.38 (1H, s), 5.66 (1H, d, J 7.0 Hz), 5.02 (1H, app d, J 7.8 Hz), 5.93 (1H, m), 4.52 (1H, ddd, J 3.8, 6.5, 10.5 Hz), 4.33 (1H, d, J 8.3 Hz), 4.18 (1H, d, J 8.3 Hz), 3.91 (1H, d, J 7.0 Hz), 2.83 (1H, d, J 4.0 Hz), 2.59 (1H, ddd, J 6.5, 9.4, 14.5 Hz), 2.33 (1H, m), 2.29 (3H, s), 2.12 (3H, d, J 1.4 Hz), 2.04 (1H, d, J 5.1 Hz), 1.89 (1H, ddd, J 2.2, 11.0, 14.4 Hz), 1.69 (3H, s), 1.62 (1H, s), 1.15 (3H, s) and 1.13 (3H, s).

10-allylcarbamoyl-10-DAB. mp 165–170° C.; $[\alpha]_{Hg}$ −80.0° (CHCl$_3$, c=0.25); $^1$H NMR(500MHz, CDCl$_3$) δ 8.12 (2H, d, J 7.3 Hz), 7.62 (1H, m), 7.51–7.48 (2H, m), 6.27 (1H, s), 5.89 (1H, m), 5.62 (1H, d, J 6.7 Hz), 5.31 (1H, s), 5.19 (1H, d, J 9.8 Hz), 5.08 (1H, m), 5.00 (1H, d, J 7.9 Hz), 4.90 (1H, m), 4.49 (1H, ddd, J, 3.7, 6.1, 10.4 Hz), 4.31 (1H, d, J 8.5 Hz), 4.17 (1H, d, J 8.5 Hz), 3.88–3.86 (2H, m), 3.03 (1H, d, J 3.7 Hz), 2.55 (1H, ddd, J 6.7, 9.8, 15.9 Hz), 2.30 (1H, m), 2.29 (3H, s), 2.08 (3H, s), 2.06 ( 1H, app d, J 4.9 Hz), 1.87 (1H, ddd, J 1.8, 11.0, 14.0 Hz), 1.67 (3H, s), 1.58 (1H, s) and 1.09 (6H, s); Anal. Calcd. for $C_{33}H_{40}NO_{11}$: C, 63.15; H, 6.58 Found: C, 61.73; H, 6.45.

E. Selective Silylation of a C(10) Hydroxyl Group

10-TMS-10-DAB. To a solution of 10-DAB (100 mg, 0.18 mmol) in THF (10 mL) at 0° C. was slowly added N, O-bis(trimethylsilyl)trifluoroacetamide (1.0 mL, 3.7 mmol, 20 equiv) under N$_2$. The reaction mixture was stirred at 0° C. for 5 h. EtOAc (20 mL) was added, and the solution was filtered through a short column of silica gel. The silica gel was washed with EtOAc (100 mL), and the solution was concentrated under reduced pressure. The residue was purified by flash column chromatography using EtOAc: hexanes (1:1) as the eluent and dried in vacuo overnight to give 10-TMS-10-DAB as a white solid: yield, 103 mg (91%). mp 189–191° C.; $[\alpha]_{Hg}$ −70° (CHCl$_3$, c=0.55); $^1$H NMR (400 MHz, CDCl$_3$) δ 0.18(s, 9 H, Me$_3$Si), 1.06(s, 3 H, Me17), 1.16(s, 3 H, Me16), 1.31(d, J=8.6 Hz, 1 H, 7-OH), 1.56(s, 1 H, 1-OH), 1.68(s, 3 H, Me19), 1.79(ddd, J=14.4, 11.1, 2.1 Hz, 1 H, H6b), 1.97(d, J=4.9 Hz, 1 H, 13-OH), 2.03(d, J=1.3 Hz, 3 H, Me18), 2.27(m, 2 H, H14a, H14b), 2.28(s, 3 H, 4-Ac), 2.58(ddd, J=14.4, 9.6, 7.5 Hz, 1 H, H6a), 4.01(d, J=7.2 Hz, 1 H, H3), 4.16(d, J=8.2 Hz, 1 H, H20b), 4.25(ddd, J=11.1, 8.6, 7.5 Hz, 1 H, H7), 4.30(d, J=8.2 Hz, 1 H, H20a), 4.84(m, 1 H, H13), 4.97(dd, J=9.6, 2.1 Hz, 1 H, H5), 5.27(s, 1 H, H10), 5.64(d, J=7.2 Hz, 1 H, H2), 7.47(dd, J=8.2, 7.5 Hz, 2 H, benzoate, m), 7.60(tt, J=7.5, 1.2 Hz, 1 H, benzoate, p), 8.11(dd, J=8.2, 1.2 Hz, 2 H, benzoate, o) ppm. 13C NMR (75 MHz, CDCl$_3$) δ 0.2(Me$_3$S), 9.7(Me(19)), 14.4(Me(18)), 19.6(4-Ac), 22.4, 26.6(Me16, Me17), 37.1(C(6)), 38.6(C (14)), 42.6(C(15)), 47.2(C(3)), 57.8(C(8)), 68.0(C(13)), 72.0, 75.1, 76.1, 76.8(C(7), C(2), C(10), C(20)), 78.9(C(1)), 81.2(C(4)), 84.3(C(5)), 128.8, 130.3, 133.7(benzoate), 137.0 (C(11)), 139.0(C(12)), 167.4(benzoate), 171.0(4-Ac), 209.5 (C(9))ppm. Anal. Calcd for $C_{32}H_{44}O_{10}Si$. ½H$_2$O: C, 61.42; H, 7.25. Found: C, 61.61; H, 7.12.

10-TES-10-DAB. To a solution of 10-DAB (85 mg, 0.16 mmol) in THF (3 mL) at 0° C. was slowly added N, O-bis(triethylsilyl)trifluoroacetamide (484 mL, 1.56 mmol, 10 equiv), and a catalytic amount of LiHMDS/THF solution (1 M, 5 mL, 0.005 mmol), respectively, under N$_2$. The reaction mixture was stirred at 0° C. for 5 min. EtOAc (10 mL) was added, and the solution was filtered through a short column of silica gel. The silica gel was washed with EtOAc (100 mL), and the solution was concentrated under reduced pressure. The residue was purified by flash column chromatography using EtOAc: hexanes (1:2) as the eluent and dried in vacuo overnight to give the 10-TES-10-DAB as a white solid: yield, 98 mg (95%). mp 234–235° C. dec; $[\alpha]_{Hg}$ −69° (CHCl$_3$, c=0.95); IR 3690, 2958, 1714, 1602 cm$^{-1}$; $^1$H NMR (500 MHz, CDCl$_3$) δ 0.68(m, 6 H, (CH$_3$CH$_2$)$_3$Si), 1.00(t, J=7.9, 9 H, (CH3CH$_2$)$_3$Si), 1.08(s, 3 H, Me17), 1.19(s, 3 H, Me16), 1.29(d, J=8.4 Hz, 1 H, 7-OH), 1.55(s, 1 H, 1-OH), 1.69(s, 3 H, Me19), 1.79(ddd, J=14.4, 11.0, 2.0 Hz, 1 H, H6b), 1.92(d, J=5.0 Hz, 1 H, 13-OH), 2.03(d, J=1.0 Hz, 3 H, Me18), 2.27(s, 3 H, 4-Ac), 2.29(m, 2 H, H14a, H14b), 2.59(ddd, J=14.4, 9.5, 6.7 Hz, 1 H, H6a), 4.02(d, J=7.2 Hz, 1 H, H3), 4.18(d, J=8.5 Hz, 1 H, H20b), 4.23(ddd, J=11.0, 8.4, 6.7 Hz, 1 H, H7), 4.30(d, J=8.5 Hz, 1 H, H20a), 4.86(m, 1 H, H13), 4.97(dd, J=9.5, 2.0 Hz, 1 H, H5), 5.28(s, 1 H, H10), 5.66(d, J=7.2 Hz, 1 H, H2), 7.47(dd, J=7.9, 7.9 Hz, 2 H, benzoate, m), 7.59(tt, J=7.9, 1.0 Hz, 1 H, benzoate, p), 8.11(dd, J=7.9, 1.0 Hz, 2 H, benzoate, o)ppm. 13C NMR (75 MHz, CDCl$_3$) δ 4.9, 6.5(TES), 9.7(Me(19)), 14.3(Me(18)), 19.6(4-Ac), 22.4, 26.6(Me16, Me17), 37.1(C(6)), 38.6(C (14)), 42.6(C(15)), 47.3(C(3)), 57.9(C(8)), 67.9(C(13)), 71.9, 75.1, 76.1, 76.7(C(7), C(2), C(10), C(20)), 78.9(C(1)), 81.2(C(4)), 84.3(C(5)), 128.7, 129.9, 130.3, 133.7 (benzoate), 137.0(C(11)), 138.8(C(12)), 167.4(benzoate), 171.0(4-Ac), 209.5(C(9)) ppm. Anal. Calcd for $C_{35}H_{50}O_{10}Si$ H$_2$O: C, 62.11; H, 7.74. Found: C, 62.45; H, 7.74.

EXAMPLE 2

General Procedure for the Preparation of 7-silyl-10-TES-10-DAB. To a solution of 7-triethylsilyl-10-DAB, 7-t-butyldimethylsilyl-10-DAB, or 7-dimethylisopropylsilyl-10-DAB in THF at 0° C. was slowly added N, O-bis (triethylsilyl)trifluoroacetamide (5 equiv), and a catalytic amount of LiHMDS/THF solution (5 mol %), respectively, under N$_2$. The reaction mixture was stirred at 0° C. for 15 min. EtOAc (10 mL) was added, and the solution was filtered through a short column of silica gel. The silica gel was washed with EtOAc (100 mL), and the solution was concentrated under reduced pressure. The residue was purified by flash column chromatography using EtOAc: hexanes (1:2) as the eluent and dried in vacuo overnight to give, respectively, 7,10-bis(triethylsilyl)-10-DAB (95% yield), 7-t-butyldimethylsilyl- 10-triethylsilyl-10-DAB (98% yield), or 7-dimethylisopropylsilyl-10-triethylsilyl-10-DAB (94% yield).

7-Dimethylphenylsilyl-10-TBS-10-DAB. To a solution of 7-dimethylphenylsilyl-10-DAB (35 mg, 0.052 mmol) in THF (2 mL) at 0 OC was added N,O-bis(t-butyldimethylsilyl)trifluoroacetamide (337 μL, 1.09 mmol, 20 equiv), and a catalytic amount of LiHMDS/THF solution (1 M, 6 μL, 0.006 mmol), respectively, under $N_2$. The reaction mixture was stirred at 0° C. for 4 h, then warmed to room temperature for an additional 4 h. EtOAc (10 mL) was added, and the solution was filtered through a short column of silica gel. The silica gel was washed with EtOAc (100 mL), and the solution was concentrated under reduced pressure. The residue was purified by flash column chromatography using EtOAc: hexanes (1:2) as the eluent and dried in vacuo overnight to give 39 mg (92% yield) of 7-dimethylphenylsilyl-10-t-butyldimetylsilyl-10-DAB.

EXAMPLE 3

Selective Silylation of a C(7) Hydroxyl Group

7-TBS-10-DAB. To a mixture of 10-DAB (38 mg, 0.070 mmol), imidazole (190 mg, 2.79 mmol, 40 equiv), and tert-butyldimethylsilyl chloride (210 mg, 1.40 mmol, 20 equiv) was added DMF (0.1 mL) at room temperature under $N_2$. The reaction mixture was vigorously stirred at room temperature for 24 h. EtOAc (20 mL) was added, and the solution was filtered through a short column of silica gel. The silica gel was washed with EtOAc (200 mL), and the solution was concentrated under reduced pressure. The residue was purified by flash column chromatography using 10% EtOAc—$CH_2Cl_2$ as the eluent and dried in vacuo overnight to give 7-TBS-10-DAB as a white solid: yield, 41 mg (90%). mp 222–223° C.; $[\alpha]_{Hg}$ −51° ($CHCl_3$, c=0.36); $^1H$ NMR (400 MHz, $CDCl_3$) δ 0.05, 0.06(2 s, 6 H, $Me_2Si$), 0.83(s, 9 H, $Me_3C$), 1.09(s, 6 H, Me16, Me17), 1.57(s, 1 H, 1-OH), 1.75(s, 3 H, Me19), 1.87(ddd, J=14.4, 10.6, 2.0 Hz, 1 H, H6b), 2.01(d, J=5.0 Hz, 1 H, 13-OH), 2.09(d, J=1.3, 3 H, Me18), 2.28(m, 2 H, H14a, H14b), 2.29(s, 3 H, 4-Ac), 2.46(ddd, J=14.4, 9.6, 6.7 Hz, 1 H, H6a), 3.96(d, J=6.9 Hz, 1 H, H3), 4.16(d, J=8.3 Hz, 1 H, H20b), 4.24(d, J=2.2 Hz, 1 H, 10-OH), 4.31(d, J=8.3 Hz, 1 H, H20a), 4.38(dd, J=10.6, 6.7 Hz, 1 H, H7), 4.88(m, 1 H, H13), 4.96(dd, J=9.6, 2.0 Hz, 1 H, H5), 5.15(d, J=2.0 Hz, 1 H, H10), 5.60(d, J=6.9 Hz, 1 H, H2), 7.47(dd, J=8.1, 7.5 Hz, 2 H, benzoate, m), 7.60(tt, J=7.5, 1.3 Hz, 1 H, benzoate, p), 8.10(d, J=8.1, 1.3 Hz, 2 H, benzoate, o) ppm. $^{13}C$ NMR (75 MHz, $CDCl_3$) δ −5.8, −3.8($Me_2Si$), 9.7(Me(19)), 14.8(Me(18)), 17.6($Me_3C$), 19.3 (4-Ac), 22.4, 26.7(Me16, Me17), 25.4($Me_3C$), 37.4(C(6)), 38.7(C(14)), 42.7(C(15)), 47.0(C(3)), 58.0(C(8)), 68.0(C (13)), 73.1, 74.7, 75.0(C(7), C(2), C(10), C(20)), 78.9(C(1)), 80.9(C(4)), 84.3(C(5)), 128.8, 129.8, 130.3, 133.8 (benzoate), 135.7(C(11)), 141.9(C(12)), 167.4(benzoate), 171.2(4-Ac), 210.8(C(9))ppm. Anal. Calcd for $C_{35}H_{50}O_{10}Si$: C, 63.80; H, 7.65. Found: C, 63.72; H, 7.70.

7-Dimethylphenylsilyl-10-DAB. To a THF (3 mL) solution of 10-DAB (54 mg, 0.099 mmol) at −20° C. was added pyridine (0.6 mL), dimethylphenylsilyl chloride (250 mL, 1.49 mmol, 15 equiv) under $N_2$. The reaction mixture was stirred at −20° C. for 2 h. EtOAc (10 mL) and saturated $NaHCO_3$ aqueous solution (0.5 mL) was added, and the solution was quickly filtered through a short column of silica gel. The silica gel was washed with EtOAc (100 mL), and the solution was concentrated under reduced pressure. The residue was purified by flash column chromatography using EtOAc: $CH_2Cl_2$ (1:10) as the eluent and dried overnight in vacuo to give 7-dimethylphenylsilyl-10-DAB as a white solid: yield, 62 mg (92%). mp 219–220° C.; $[\alpha]_{Hg}$ −28° ($CHCl_3$, c=0.27); $^1H$ NMR (400 MHz, $CDCl_3$) δ 0.35, 0.37(2 s, 6 H, $Me_2Si$), 1.05(s, 3 H, Me17), 1.06(s, 3 H, Me16), 1.54(s, 1 H, 1-OH), 1.73(d, J=1.1, 3 H, Me18), 1.76(s, 3 H, Me19), 1.90(ddd, J=14.4, 10.6, 2.1 Hz, 1 H, H6b), 1.93(d, J=5.0 Hz, 1 H, 13-OH), 2.23(m, 2 H, H14a, H14b), 2.25(s, 3 H, 4-Ac), 2.43(ddd, J=14.4, 9.6, 6.8 Hz, 1 H, H6a), 3.86(d, J=7.0 Hz, 1 H, H3), 4.10(d, J=2.1 Hz, 1 H, 10-OH), 4.16(d, J=8.3 Hz, 1 H, H20b), 4.28(d, J 8.3 Hz, 1 H, H20a), 4.31(dd, J=10.6, 6.8 Hz, 1 H, H7), 4.81(m, 1 H, H13), 4.84(d, J=2.1 Hz, 1 H, H10), 4.90(dd, J=9.6, 2.1 Hz, 1 H, H5), 5.59(d, J=7.0 Hz, 1 H, H2), 7.41, 7.53(2 m, 5 H, $C_6H_5$), 7.46(dd, J=8.0, 7.5 Hz, 2 H, benzoate, m), 7.55(tt, J=7.5, 1.2 Hz, 1 H, benzoate, p), 8.09(d, J=8.0, 1.2 Hz, 2 H, benzoate, o) ppm. $^{13}C$ NMR (75 MHz, $CDCl_3$) δ −1.8, −1.1($Me_2Si$), 9.8(Me(19)), 14.4(Me(18)), 19.4(4-Ac), 22.3, 26.7(Me16, Me17), 37.2(C(6)), 38.6(C(14)), 42.6(C(15)), 46.7(C(3)), 58.0(C(8)), 68.0(C(13)), 73.2, 74.7, 75.0(C(7), C(2), C(10), C(20)), 78.8(C(1)), 80.8(C(4)), 84.3(C(5)), 128.3, 128.8, 129.8, 130.2, 130.3, 133.65, 133.74(PhSi, benzoate), 135.4(C(11)), 142.1(C(12)), 167.4(benzoate), 171.0(4-Ac), 210.9(C(9))ppm. Anal. Calcd for $C_{37}H_{46}O_{10}Si$. ½$H_2O$: C, 64.61; H, 6.89. Found: C, 64.72; H, 6.81.

7-Dimethylisopropylsilyl-10-DAB. To a solution of 10-DAB (97 mg, 0.18 mmol) in pyridine (1 mL) at −10° C. was added dimethylisopropylsilyl chloride (580 mL, 3.57 mmol, 20 equiv) under $N_2$. The reaction mixture was stirred at −10° C. for 3 h. EtOAc (10 mL) was added, and the solution was quickly filtered through a short column of silica gel. The silica gel was washed with EtOAc (150 mL), and the solution was concentrated under reduced pressure. The residue was purified by flash column chromatography using EtOAc: hexanes (1:2) as the eluent to give 7-dimethylisopropyl-10-DAB as a white solid: yield, 107 mg (93%). mp 229–230° C.; $[\alpha]_{Hg}$ −56° ($CHCl_3$, c=0.62); $^1H$ NMR (400 MHz, $CDCl_3$) δ 0.05, 0.06(2 s, 6 H, $Me_2Si$), 0.70(m, 1 H, CHSi), 0.90, 0.92(2 dd, J=7.4, 1.7, 6 H, $Me_2CH$), 1.09(s, 6 H, Me16, Me17), 1.56(s, 1 H, 1-OH), 1.74(s, 3 H, Me19), 1.89(ddd, J=14.4, 10.6, 2.1 Hz, 1 H, H6b), 1.99(d, J=5.0 Hz, 1 H, 13-OH), 2.09(d, J=1.4, 3 H, Me18), 2.28(d, J=7.9, 2 H, H14a, H14b), 2.29(s, 3 H, 4-Ac), 2.44(ddd, J=14.4, 9.7, 6.7 Hz, 1 H, H6a), 3.96(d, J=7.3 Hz, 1 H, H3), 4.17(d, J=8.3 Hz, 1 H, H20b), 4.24(d, J=2.2 Hz, 1 H, 10-OH), 4.31(d, J=8.3 Hz, 1 H, H20a), 4.38(dd, J=10.6, 6.7 Hz, 1 H, H7), 4.85(m, 1 H, H13), 4.95(dd, J=9.7, 2.1 Hz, 1 H, H5), 5.15(d, J=2.2 Hz, 1 H, H10), 5.61(d, J=7.3 Hz, 1 H, H2), 7.47(dd, J=8.2, 7.5 Hz, 2 H, benzoate, m), 7.60(tt, J=7.5, 1.4 Hz, 1 H, benzoate, p), 8.10(d, J=8.2, 1.4 Hz, 2 H, benzoate, o) ppm. $^{13}C$ NMR (75 MHz, $CDCl_3$) δ −4.6, −3.3($Me_2Si$), 9.7(Me(19)), 14.8, 14.9 (CHSi, Me(18)), 16.4, 16.5($Me_2CH$), 19.4(4-Ac), 22.4, 26.7(Me16, Me17), 37.3(C (6)), 38.7(C(14)), 42.7(C(15)), 47.0(C(3)), 58.0(C(8)), 68.0 (C(13)), 73.1, 74.7, 75.0(C(7), C(2), C(10), C(20)), 78.9(C (1)), 80.9(C(4)), 84.3(C(5)), 128.8, 129.8, 130.3, 133.7 (benzoate), 135.7(C(11)), 142.0(C(12)), 167.4(benzoate), 171.1(4-Ac), 210.8(C(9)) ppm. Anal. Calcd for $C_{34}H_{48}O_{10}Si$. $H_2O$: C, 61.61; H, 7.60. Found: C, 61.30; H, 7.35.

7-Tribenzylsilyl-10-DAB. To a mixture of 10-DAB (62 mg, 0.11 mmol), imidazole (280 mg, 4.11 mmol, 36 equiv) and tribenzylsilyl chloride (364 mg, 1.14 mmol, 10 equiv) was added DMF (0.4 mL) under $N_2$. The reaction mixture was stirred at room temperature for 3 h. EtOAc (30 mL) was added, and the solution was filtered through a short column of silica gel. The silica gel was washed with EtOAc (150 mL), and the solution was concentrated under reduced pressure. The residue was purified twice by flash column chromatography, first time using EtOAc: hexanes (1:2) as the eluent, second time using EtOAc: $CH_2Cl_2$ as the eluent, and dried overnight in vacuo to give the 7-tribenzylsilyl-10-DAB as a white solid: yield, 88 mg (91%). mp 161–163° C.; IR 3690, 2928, 2890, 1712, 1600 $cm^{-1}$; $[\alpha]_{Hg}$ −46° ($CHCl_3$, c=0.46); $^1H$ NMR (400 MHz, $CDCl_3$) δ 1.10(s, 3 H, Me17, Me16), 1.56(s, 1 H, 1-OH), 1.71(ddd, J=14.2, 10.9, 2.0 Hz, 1 H, H6b), 1.74(s, 3 H, Me19), 2.00(d, J=5.1 Hz, 1 H, 13-OH), 2.07(ddd, J=14.2, 9.6, 6.6 Hz, 1 H, H6a), 2.10(d, J=1.2, 3 H, Me18), 2.12(s, 6 H, (PhCH$_2$)$_3$Si), 2.27(d, J=7.5 Hz, 2 H, H14a, H14b), 2.27(s, 3 H, 4-Ac), 3.99(d, J=7.0 Hz, 1 H, H3), 4.16(d, J=8.5 Hz, 1 H, H20b), 4.18(d, J=2.2 Hz, 1 H, 10-OH), 4.28(d, J=8.5 Hz, 1 H, H20a), 4.58(dd, J=10.9, 6.6 Hz, 1 H, H7), 4.81(dd, J=9.6, 2.0 Hz, 1 H, H5), 4.89(m, 1 H, H13), 5.21(d, J=2.2 Hz, 1 H, H10), 5.61(d, J=7.0 Hz, 1 H, H2), 6.93, 7.09, 7.20(3 m, 15 H, (PhCH$_2$)$_3$Si), 7.48(dd, J=8.1, 7.5 Hz, 2 H, benzoate, m), 7.61(tt, J=7.5, 1.3 Hz, 1 H, benzoate, p), 8.10(d, J=8.1, 1.3 Hz, 2 H, benzoate, o) ppm. $^{13}$C NMR (75 MHz, CDCl$_3$) δ 9.9(Me(19)), 15.0(Me(18)), 19.5(4-Ac), 22.4, 26.7(Me16, Me17), 23.6(Si(CH$_2$Ph)$_3$), 36.9(C(6)), 38.7(C(14)), 42.7(C(15)), 46.8(C(3)), 58.0(C(8)), 68.0(C(13)), 74.4, 74.9, 75.0(C(7), C(2), C(10), C(20)), 78.8(C(1)), 80.8(C(4)), 84.1(C(5)), 124.9, 128.7, 128.8, 129.1, 129.8, 130.3, 133.8, 137.8(Si(CH$_2$Ph)$_3$, benzoate), 135.5(C(11)), 142.2(C(12)), 167.4(benzoate), 170.9(4-Ac), 210.8(C(9))ppm. Anal. Calcd for C$_{50}$H$_{56}$O$_{10}$Si. ½H$_2$O: C, 70.32; H, 6.73. Found: C, 70.11; H, 6.57.

EXAMPLE 4

Selective Acylation of 10-acyl-10-DAB

10-Alloc-7-p-Nitrobenzyloxycarbonyl-10-DAB. To a mixture of 10-alloc-10-DAB (33 mg, 0.053 mmol) and DMAP (19.3 mg, 0.16 mmol, 3 equiv) in dichloromethane (4 mL) at 0° C. was added a dichloromethane solution (1 mL) of p-nitrobenzyl chloroformate (23 mL, 0.11 mmol, 2 equiv) under N$_2$. The reaction mixture was stirred at 0° C. for 4 h. EtOAc (10 mL) was added, the solution was quickly filtered through a short column of silica gel. The silica gel was washed with EtOAc (100 mL), and the solution was concentrated under reduced pressure. The residue was purified by flash column chromatography using EtOAc: hexanes (1:2) as the eluent and dried overnight in vacuo to give 10-alloc-7-p-nitrobenzyloxycarbonyl-10-DAB as a colorless solid: yield, 34 mg (92%).

7-Benzyloxycarbonyl baccatin III. To a stirred solution of baccatin III (100 mg , 0.168 mmol) in methylene chloride under N$_2$ at room temperature was added 4-dimethylaminopyridine (204 mg, 1.68 mmol) followed by addition of benzyl chloroformate (240 mL, 1.68 mmol). The reaction mixture was stirred at room temperature and the progress of the reaction was monitored by TLC. After about 4 h the reaction was complete The mixture was diluted with EtOAc (10 mL) and was transferred to a separatory funnel containing 50 mL of a 50% EtOAc/Hexanes. The mixture was washed with saturated sodium bicarbonate and the organic layer was separated. The aqueous layer was washed with 20 mL of 50% EtOAc/Hexanes. The combined organic layers were washed with brine, dried over MgSO$_4$, and concentrated under reduced pressure. The crude product was passed through a short column to give 115 mg (95%) of a white solid m.p. 245–248° C.;[α]$^{25}_D$ −60.5° C. (C=0.007, CHCl$_3$). $^1$H NMR (CDCl$_3$, 400 MHz) δ 8.10(d, J=9.6 Hz, 2H, o-benzoate), 7.60–6.8 (m, 8H, benzoate, Bn), 6.45(s, 1H, H10), 5.63(d, J=6.9 Hz, 1H, H2b), 5.56 (dd, J=10.6, 7.2 Hz, 1H H7), 5.56(dd, J=18.5, 12.0 Hz, 2H, Bn), 4.97(d, J=10.6, 1H, H5), 4.87(m, 1H, H13), 4.31(d,J=10.5, 1H, H20a), 4.15 (d, J=10.5, 1H, H20b), 4.02(d, J=6.9, 1H, H3), 2.61(m, 1H, H6a), 2.30(m, 2H, H14' s), 2.29(s, 3H, 4Ac), 2.18(s, 3H, 10Ac), 2.15(br s, 3H, Me18), 2.08(d, J=5.2 Hz, 13OH), 1.94(m, 1H, 6b), 1.79(s, 3H, Me19), 1.58(s, 1H, 1OH), 1.14(s, 3H, Me16), 1.09(s, 3H, Me17).

7-Allyloxycarbonyl baccatin III. To a stirred solution of baccatin III (30 mg , 0.051 mmol) in methylene chloride (1 mL) under N$_2$ at room temperature, was added 4-dimethylaminopyridine (62.3 mg, 0.51 mmol) followed by addition of allyl chloroformate(54 mL, 0.51 mmol).The reaction mixture was stirred at room temperature and the progress of the reaction was followed by TLC. After about 1.5 h the reaction was complete The mixture was diluted by EtOAc (5 mL) and was transferred to a separatory funnel containing 50 mL of a 50% EtOAc/Hexanes. The mixture was washed with saturated sodium bicarbonate and the organic layer was separated. The aqueous layer was washed with 10 mL of 50% EtOAc/Hexanes, the combined organic layers were washed with brine, dried over MgSO$_4$, and concentrated under reduced pressure. The crude product was passed through a short column to give 33.1 mg (97%) of a white solid m.p. 239–244° C; [α]$^{25}_D$ −61.5 c (0.01, CHCl$_3$) 1H NMR (CDCl$_3$, 500 MHz) δ 8.12(d, J=8.3 Hz, 2H, o—benzoate), 7.66–7.45 (m, 3H, benzoate), 6.43(s, 1H, H10), 5.97(m, 1H, int. allyl), 5.64(d, J=7.0 Hz, 1H, H2b), 5.54 (dd, J=10.5, 7.0 Hz, 1H, H7), 5.28(m, 2H, ext. allyl), 4.97(d, J=9.6 Hz, 1H, H5), 4.87(m, 1H, H13), 4.67(m, 2H, CH2allyl), 4.31(d, J=8.5 Hz, 1H, H20a), 4.17 (d, J=8.5, 1H, H20b), 4.02(d, J=7.0, 1H, H3), 2.64(m, 1H, H6a), 2.30(d, J=8.0 Hz, 2H, H14' s), 2.29(s, 3H, 4Ac), 2.16(s, 3H, 10Ac), 2.15(br s, 3H, Me18), 2.01(d, J=5 Hz, 13OH), 1.96(m, 1H, 6b), 1.81(s, 3H, Me19), 1.58(s, 1H, 10H), 1.15(s, 3H, Me16), 1.02(s, 3H, Me17).

EXAMPLE 5

Selective Ketalization of 10-acyl-10-DAB

7-MOP baccatin III. To a solution of baccatin III (101 mg, 0.172 mmol) in THF (8 mL) at −20° C. was added 2-methoxypropene (0.66 mL, 6.89 mmol, 40 equiv), followed by the addition of a catalytic amount of toluenesulfonic acid (0.1 M solution in THF, 43 μL, 0.004 mmol, 0.025 equiv) under N$_2$. The reaction mixture was stirred at −20° C. for 3 h. TLC analysis indicated complete consumption of the starting material and the formation of desired product as the only major product. Triethylamine (0.5 mL) was added, and the solution was warmed to room temperature, diluted with EtOAc (100 mL), washed with saturated aqueous NaHCO$_3$ solution, dried over Na$_2$SO$_4$, and concentrated under reduced pressure. The residue was dried in vacuo overnight to give 112 mg (99%) of crude product. Recrystallization of the crude product from EtOAc/hexanes gave 105 mg (93%) of 7-MOP baccatin III as a white crystal, mp 181–183° C.; $^1$H NMR (500 MHz, C$_6$D$_6$) δ 1.01 (s, 3 H, Me17), 1.11(br s, 1 H, 13-OH), 1.28(s, 3 H, Me16), 1.39, 1.78(2 s, 6 H, Me$_2$CO), 1.62(s, 1 H, 1-OH), 1.78(s, 3 H, 10-Ac), 1.92(s, 3 H, 4-Ac), 2.09(s, 3 H, Me18), 2.12(s, 3 H, Me19), 2.14(ddd, J=15.0, 10.9, 2.2 Hz, 1 H, H6b), 2.18(dd, J=15.6, 9.4 Hz, 1 H, H14b), 2.31(dd, J=15.6, 7.0 Hz, 1 H, H14b), 2.97(s, 3 H, MeO), 3.15(ddd, J=15.0, 9.9, 6.7 Hz, 1 H, H6a), 4.08(d, J=7.0 Hz, 1 H, H3), 4.24(m, 1 H, H13), 4.33(d, J=8.3 Hz, 1 H, H20b), 4.41(d, J=8.3 Hz, 1 H, H20a), 4.78(dd, J=10.9, 6.7 Hz, 1 H, H7), 4.97(dd, J=9.9, 2.2 Hz, 1 H, H5), 5.95(d, J=7.0 Hz, 1 H, H2), 6.79(s, 1 H, H10), 7.15(m, 3 H, benzoate, m, p), 8.28(d, J=8.0 Hz, 2 H, benzoate, o) ppm; Anal. Calcd for C$_3$H$_{46}$O$_{12}$: C, 63.82; H, 7.04. Found: C, 63.72; H, 7.07.

EXAMPLE 6

Selective Acylation of 10-silyl-10-DAB

7-Acetyl-10-TES-10-DAB. To a stirred solution of 10-TES-10-DAB (65 mg, 0.098 mmol) in dichloromethane (4 ml) at 0° C. under N$_2$, was added DMAP (36 mg, 0.296 mmol, 3 equiv), followed by addition of acetic anhydride (14 mL, 0.148 mmol, 1.5 equiv). The reaction mixture was stirred at 0° C. for 4.5 hrs and the TLC analysis indicated the complete consumption of starting material. The reaction mixture was then filtered through a short pad of silica gel, the silica gel was washed with EtOAc (100 mL) and the solution was concentrated under reduced pressure. The residue was purified by flash chromatography using EtOAc:hexanes (1:2) as the eluent and dried in vaccuo overnight to give the 7-acetyl-10-TES-10-DAB: yield, 65.7 mg (95%). $^1$H NMR (CDCl$_3$, 400 MHz), δ 0.60(m, 6 H, (CH$_3$CH$_2$)$_3$Si), 0.97(t, J=7.9 Hz, 9 H, (CH$_3$CH$_2$)$_3$Si), 1.05(s, 3 H, Me17), 1.18(s, 3 H, Me16), 1.56(s, 1 H, 1-OH), 1.79(s, 3 H, Me19), 1.83(ddd, J=14.5, 10.3, 2.0 Hz, 1 H, H6b), 1.97(m, 1 H, 13-OH), 2.00(s, 3 h, 7-Ac), 2.07(d, J=1.3 Hz, 3 H, Me18), 2.26(m, 2 H, H14a, H14b), 2.29(s, 3 H, 4-Ac), 2.57(ddd, J=14.5, 9.5, 7.3 Hz, 1 H, H6a), 4.06(d, J=7.0 Hz, 1 H, H3), 4.17(d, J=8.2 Hz, 1 H, H20b), 4.31(d, J=8.2 Hz, 1 H, H20a), 4.84(m, 1 H, H13), 4.94(dd, J=9.5, 2.0 Hz, 1 H, H5), 5.29(s, 1 H, H10), 5.46(dd, J=10.3, 7.3 Hz, 1 H, H7), 5.65(d, J=7.0 Hz, 1 H, H2), 7.47(m, 2 H, benzoate, m), 7.60(m, 1 H, benzoate, p), 8.11(d, J=8.0 Hz, 2 H, benzoate, o) ppm.

7-Troc-10-TES-10-DAB. To a mixture of 10-TES-10-DAB (40 mg, 0.061 mmol) and DMAP (72 mg, 0.61 mmol, 10 equiv) in dichloromethane (2 mL) was added trichloroethyl chloroformate (24 mL, 0.184 mmol, 3 equiv) under N$_2$. The reaction mixture was stirred at room temperature and the progress of the reaction was monitored by TLC analysis. After 0.5 h, TLC analysis indicated almost complete disappearance of 10-TES-10-DAB and the formation of the product as the only major spot. Methanol (5 mL) was added, and the solution was quickly filtered through a short column of silica gel. The silica gel was washed with EtOAc (100 mL), and the solution was concentrated under reduced pressure. The residue was purified by flash chromatography using EtOAc: CH$_2$Cl$_2$ (1:10) as the eluent and dried in vacuo overnight to give 7-Troc-10-TES- 10-DAB as a white solid: yield, 49 mg (97%); $^1$H NMR (500 MHz, CDCl$_3$) δ 0.61(m, 6 H, (CH$_3$CH$_2$)$_3$Si), 0.99(t, J=7.9, 9 H, (CH$_3$CH$_2$)$_3$Si), 1.08(s, 3 H, Me17), 1.20(s, 3 H, Me16), 1.56(s, 1 H, 1-OH), 1.84(s, 3 H, Me19), 1.96(d, J=4.9 Hz, 1 H, 13-OH), 2.01 (ddd, J=14.4, 10.5, 2.0 Hz, 1 H, H6b), 2.08(d, J=1.2, 3 H, Me18), 2.29(m, 2 H, H14a, H14b), 2.29(s, 3 H. 4-Ac), 2.68(ddd, J=14.4, 9.5, 7.3 Hz, 1 H, H6a), 4.08(d, J=6.7 Hz, 1 H, H3), 4.18(d, J=8.5 Hz, 1 H, H20b), 4.32(d, J=8.5 Hz, 1 H, H20a), 4.43(d, J=11.9 Hz, 1 H, CHH'OC(O)), 4.86(m, 1 H, H13), 4.95(dd, J=9.3, 2.0 Hz, 1 H, H5), 4.98(d, J=11.9 Hz, 1 H, CHH'OC(O)), 5.33(s, 1 H, H10), 5.37(dd, J=10.5, 7.3 Hz, 1 H, H7), 5.67(d, J=6.7 Hz, 1 H, H2), 7.48(dd, J=7.9, 7.3 Hz, 2 H, benzoate, m), 7.60(tt, J=7.3, 1.2 Hz, 1 H, benzoate, p), 8.11(dd, J=7.9, 1.2 Hz, 2 H, benzoate, o)ppm.

7-p-Ni trobenzyloxycarbonyl -10-TES-10-DAB. To a mixture of 10-TES-10-DAB (40 mg, 0.061 mmol) and DMAP (72 mg, 0.61 mmol, 10 equiv) in dry chloroform (2 mL) was added p-nitrobenzyl chloroformate (131 mg, 0.61 mmol, 10 equiv) under N$_2$. The reaction mixture was stirred at room temperature and the progress of the reaction was monitored by TLC analysis. After 45 min, TLC analysis indicated almost complete disappearance of 10-TES-10-DAB and the formation of the product as the only major spot. Methanol (10 mL) was added, and the solution was quickly filtered through a short column of silica gel. The silica gel was washed with EtOAc (100 mL), and the solution was concentrated under reduced pressure. The residue was purified by flash chromatography using EtOAc: CH$_2$Cl$_2$ (1:10) as the eluent and dried in vacuo overnight to give 7-p-Nitrobenzyloxycarbonyl-10-TES-10-DAB as a white solid: yield, 48.3 mg (95%); $^1$H NMR (500 MHz, CDCl$_3$) δ 0.60(m, 6 H, (CH$_3$CH$_2$) $_3$Si), 0.95(t, J=7.9, 9 H, (CH$_3$CH$_2$) $_3$Si), 1.08(s, 3 H, Me17), 1.19(s, 3 H, Me16), 1.55(s, 1 H, 1-OH), 1.83(s, 3 H, Me19), 1.93(ddd, J=14.3, 10.4, 2.2 Hz, 1 H, H6b), 1.96(d, J=4.9 Hz, 1 H, 13-OH), 2.09(d, J=1.2, 3 H, Me18), 2.29(m, 2 H, H14a, H14b), 2.29(s, 3 H, 4-Ac), 2.65(ddd, J=14.3, 9.3, 7.3 Hz, 1 H, H6a), 4.08(d, J=7.0 Hz, 1 H, H3), 4.18(d, J=8.6 Hz, 1 H, H20b), 4.31(d, J=8.6 Hz, 1 H, H20a), 4.86(m, 1 H, H13), 4.95(dd, J=9.3, 2.2 Hz, 1 H, H5), 5.06(d, J=13.4 Hz, 1 H, CHH'OC(O)), 5.31(d, J=13.4 Hz, 1 H, CHH'OC(O)), 5.33(s, 1 H, H10), 5.36(dd, J=10.4, 7.3 Hz, 1 H, H7), 5.66(d, J=7.0 Hz, 1 H, H2), 7.48(dd, J=7.4, 7.3 Hz, 2 H, benzoate, m), 7.53(d, J=8.9 Hz, 2 H, NO$_2$C$_6$H$_4$), 7.59(tt, J=7.3, 1.2 Hz, 1 H, benzoate, p), 8.12(dd, J=7.4, 1.2 Hz, 2 H, benzoate, o), 8.23(d, J=8.9 Hz, 2 H, NO$_2$C$_6$H$_4$) ppm.

7-Cbz-10-TES-10-DAB. To a mixture of 10-TES-10-DAB (40 mg, 0.061 mmol) and DMAP (440 mg, 3.64 mmol, 60 8equiv) in dry chloroform (2 mL) was slowly added four equal aliquot of benzyl chloroformate (4×130 mL, 3.64 mmol, 60 equiv) via a syringe in a 10-min interval under N$_2$ during a period of 40 min. The reaction mixture was then stirred at room temperature and the progress of the reaction was monitored by TLC analysis. After 2 h, TLC analysis indicated almost complete disappearance of 10-TES-10-DAB and the formation of the product as the only major spot. Methanol (10 mL) was added, and the solution was poured into ethyl acetate (100 mL), washed with a saturated aqueous NaHCO$_3$ solution, H$_2$O, and brine. The solution was dried over Na$_2$SO$_4$, concentrated under reduced pressure. The residue was purified by flash chromatography using EtOAc: CH$_2$Cl$_2$ (1:10) as the eluent and dried in vacuo overnight to give 7-CBz-10-TES-10-DAB as a white solid: yield, 45 mg (93%); $^1$H NMR (500 MHz, CDCl$_3$) δ 0.62(m, 6 H, (CH$_3$CH$_2$) $_3$Si), 0.97(t, J=7.9, 9 H, (CH$_3$CH$_2$)$_3$Si), 1.07(s, 3 H, Me17), 1.20(s, 3 H, Me16), 1.55(s, 1 H, 1-OH), 1.81(s, 3 H, Me19), 1.91(ddd, J=14.3, 10.5, 2.1 Hz, 1 H, H6b), 1.96(d, J=4.9 Hz, 1 H, 13-OH), 2.10(d, J=1.2, 3 H, Me18), 2.28(m, 2 H, H14a, H14b), 2.28(s, 3 H, 4-Ac), 2.64(ddd, J=14.3, 9.5, 7.3 Hz, 1 H, H6a), 4.08(d, J=7.0 Hz, 1 H, H3), 4.17(d, J=8.5 Hz, 1 H, H20b), 4.30(d, J=8.5 Hz, 1 H, H20a), 4.86(m, 1 H, H13), 4.95(dd, J=9.5, 2.1 Hz, 1 H, H5), 5.01(d, J=12.2 Hz, 1 H, CHH'OC(O)), 5.24(d, J=12.2 Hz, 1 H, CHH'OC(O)), 5.34(s, 1 H, H10), 5.37(dd, J=10.5, 7.3 Hz, 1 H, H7), 5.65(d, J=7.0 Hz, 1 H, H2), 7.32–7.37(m, 5 H, PhCH$_2$O), 7.47(dd, J=8.3, 7.3 Hz, 2 H, benzoate, m), 7.59(tt, J=7.3, 1.3 Hz, 1 H, benzoate, p), 8.12(dd, J=8.3, 1.3 Hz, 2 H, benzoate, o) ppm.

EXAMPLE 7

Selective silylation of 10-acyl-10-DAB 7-dimethylisopropylsilyl baccatin III. To a stirred solution of baccatin III (30 mg, 0.051 mmol) in pyridine (0.6 mL) at 0° C. under N$_2$, was added chlorodimethyl-isopropylsilane (160 uL, 1.02 mmol). The reaction mixture was stirred at that temperature and the progress of the reaction was monitored by TLC. After about 1.5 h the reaction was complete. Ethyl acetate (5 mL) was added and the solution was transferred to a separatory funnel containing 50 mL of a 50% EtOAc/Hexanes. The mixture was washed with saturated sodium bicarbonate and the organic layer was separated. The aqueous layer was extracted with 10 mL of 50% EtOAc/Hexanes and the combined organic layers were washed with saturated sodium chloride, dried over MgSO$_4$, concentrated under reduced pressure. The crude product was passed through a short silica gel column to give 33.9 mg (97%) of a white solid m.p. 204–207° C.; [α]$^{25}$D −58.6° C. (0.009, CHCl$_3$). $^1$HNMR (CDCl$_3$, 500 MHZ), δ 8.10(d,J=8.4 Hz,2H, o-benzoate), 7.60–7.20 (m, 3H, benzoate), 6.4 (s, 1H, H10), 5.64(d, J=7.1 Hz, 1H, H2b), 4.95(d, J=4.9 Hz, 1H, H5), 4.84(m, 1H, H13), 4.44(dd, J=10.4, 6.8 Hz, 1H, H7), 4.30(d, J=8.3 Hz, 1H, H20a), 4.14 (d, J=8.3 Hz, 1H, H20b), 4.15(d, J=7.2 Hz, 1H, H3), 2.49(m, 1H, H6a), 2.23(m, 2H, H14's), 2.28(s, 3H, 4Ac), 2.18(br s, 3H, Me 18), 2.17(s, 3H, 10Ac), 2.01(d, J=5.0 Hz, 13 OH), 1.86(m, 1H, 6b), 1.69(s, 3H,Me19), 1.61(s, 1H,10H), 1.20(s, 3H, Me16), 1.05(s, 3H, Me17), 0.87(d, J=7.1 Hz, 6H,i-pr), 0.73(m,1H,i-pr), 0.09(s, 6H, Me2Si).

7-dimethylphenylsilyl baccatin III. To a stirred solution of baccatin III (20 mg, 0.034 mmol) in THF (1.25 mL) at −10° C. under N$_2$, was added chlorodimethyphenylsilane (68 uL, 0.41 mmol), followed by addition of pyridine (250 mL, 3.1 mmol). The reaction mixture was stirred at that temperature and the progress of the reaction was monitored by TLC. After about one hour the reaction was complete. Ethyl acetate (5 mL) was added and the solution was transferred to a separatory funnel containing 30 mL of 50% EtOAc/Hexanes. The mixture was washed with saturated sodium bicarbonate and the organic layer was separated. The aqueous layer was extracted with 10 mL of 50% EtOAc/Hexanes and the combined organic layers were washed with saturated sodium chloride, dried over MgSO$_4$, concentrated under reduced pressure. The crude product was passed through a short silica gel column to give 24.1 mg (98%) of a white solid m.p. 210–213° C.; [α]$^{25}$ −58.3.5° C. (0.005, CHCl$_3$) $^1$H NMR (CDCl$_3$, 500 MHz) δ 8.35(d, J=8.5 Hz,2H, o-benzoate), 7.627.25(m, 8H, benzoate, phenyl), 6.42 (s,1H, H10), 5.64 (d, J=6.9 Hz, 1H, H2b), 4.84(m,1H, H5), 4.81(m, 1H, H13), 4.46 (dd, J=10.6, 6.9 Hz, 1H, H7), 4.21(d, J=8.5 Hz, 1H, H20a), 4.14 (d, J=8.5 Hz, 1H, H20b), 3.85(d, J=6.9 Hz, 1H, H3), 2.34(m, 1H, H6a), 2.26(d, J=8 Hz, 2H, H14's), 2.24(s, 3H, 4Ac), 2.15(s, 3H, 10Ac), 2.02(br d, J=1 Hz,3H, Me 18), 1.93(d, J=5 Hz, 1H,13OH), 1.77(m, 1H, 6b), 1.72(s, 3H,Me19), 1.59(s, 1H, 1OH), 1.20(s, 3H, Me16), 1.05(s, 3H, Me17), 0.446(s, 3H, Me Si), 0.335(s, 3H, Me Si).

7-dimethylphenylsilyl -10-propionyl-10-DAB. To a stirred solution of 10-propionyl-10-DAB (0.200 g, 0.333 mmol) in THF (12 mL) at −10° C., was added chlorodimethyl-phenylsilane (0.668 mL, 4.00 mmol) followed by pyridine dropwise (2.48 mL, 30.64 mmol). The reaction was stirred for 90 minutes. Ethyl acetate (20 mL) was added and the solution transferred to a separatory funnel containing 100 mL of 50% EtOAc/Hexanes. The mixture was washed with saturated sodium bicarbonate and the organic layer separated. The aqueous layer was extracted with 50% EtOAc/Hexanes (30 mL) and the combined organic extracts washed with saturated sodium chloride, dried over Na$_2$SO$_4$, concentrated in vacuo. The crude solid was then purified with flash column chromatography using 50% EtOAc/hexane as eluent to give 7-dimethylphenylsilyl-10-propionyl-10-DAB (0.242 g, 99%) as a solid. $^1$H NMR (CDCl$_{31}$ 500 MHz), δ 0.34, 0.45(2 s, 6 H, Me$_2$Si), 1.05(s, 3 H, Me17), 1.20(t, J=7.5 Hz, 3 H, CH$_3$CH$_2$), 1.21(s, 3 H, Me16), 1.60(s, 1 H, 1-OH), 1.72(s, 3 H, Me19), 1.78(ddd, J=14.5, 10.0, 2.0 Hz, 1 H, H6b), 2.04(m, 1 H, 13-OH), 2.05(s, 3 H, Me18), 2.27(m, 2 H, H14a, H14b), 2.25(s, 3 H, 4-Ac), 2.34(ddd, J=14.5, 9.5, 7.0 Hz, 1 H, H6a), 2.42, 2.49(2 dq, J=16.5, 7.5 Hz, 6 H, CH$_3$CH$_2$), 3.87(d, J=7.5 Hz, 1 H, H3), 4.14(d, J=8.0 Hz, 1 H, H20b), 4.27(d, J=8.0 Hz, 1 H, H20a), 4.47(dd, J=10.0, 7.0 Hz, 1 H, H7), 4.82(m, 1 H, H13), 4.85(dd, J=9.5, 2.0 Hz, 1 H, H5), 5.64(d, J=7.5 Hz, 1 H, H2), 6.44(s, 1 H, H10), 7.32–7.36, 7.55–7.57(2 m, 5 H, PhSi), 7.46(m, 2 H, benzoate, m), 7.59(m, 1 H, benzoate, p), 8.10(d, J=8.0 Hz, 2 H, benzoate, o) ppm.

7-Dimethylphenyl silyl -10-cyclopropanecarbonyl-10-DAB. To a solution of 10-cyclopropanecarbonyl-10-DAB (680 mg, 1.1 mmol) in THF (25 mL) were added with stirring pyridine (3.5 mL) and then chlorodimethylphenylsilane (1.8 mL, 11 mmol) at −10° C. under N$_2$. The solution was stirred till the reaction completed. Then quenched with sat. NaHCO$_3$ (20 mL). The mixture was extracted with EtOAc (2×250 mL). The combined organic layers were washed with brine (2×10 mL), dried and filtered. Concentration of the filtrate in vacuo and followed by flash chromatography (hexane:EtOAc, 4:1) gave 7-Dimethyl-phenylsilyl-10-cyclopropane-carbonyl-10-DAB (816 mg, ~100%). $^1$H NMR (CDCl$_3$, 500 MHz), δ 0.32, 0.43(2 s, 6 H, Me$_2$Si), 0.91, 1.00, 1.17(3 m, 5 H, cyclopropyl), 1.07(s, 3 H, Me17), 1.21(s, 3 H, Me16), 1.73(s, 3 H, Me19), 1.74(s, 1 H, 1-OH), 1.78(ddd, J=14.4, 10.5, 2.1 Hz, 1 H, H6b), 2.04(m, 1 H, 13-OH), 2.05(d, J=1.5 Hz, 3 H, Me18), 2.24(s, 3 H, 4-Ac), 2.26(m, 2 H, H14a, H14b), 2.34(ddd, J=14.4, 9.5, 6.7 Hz, 1 H, H6a), 3.87(d, J=7.0 Hz, 1 H, H3), 4.15(d, J=8.2 Hz, 1 H, H20b), 4.26(d, J=8.2 Hz, 1 H, H20a), 4.46(dd, J=10.5, 6.7 Hz, 1 H, H7), 4.82(m, 1 H, H13), 4.85(dd, J=9.5, 2.1 Hz, 1 H, H5), 5.65(d, J=7.0 Hz, 1 H, H2), 6.44(s, 1 H, H10), 7.32–7.36, 7.55–7.57(2 m, 5 H, PhSi), 7.46(m, 2 H, benzoate, m), 7.59(m, 1 H, benzoate, p), 8.10(d, J=8.0 Hz, 2 H, benzoate, o) ppm.

EXAMPLE 8

7-p-Nitrobenzyloxycarbonyl-10-DAB. To a THF solution (1 mL) of 10-alloc-7-p-nitrobenzyloxycarbonyl-10-DAB (34 mg, 0.048 mmol) at room temperature was added a THF solution (1 mL) of formic acid (19 mL, 0.48 mmol, 10 equiv) and butylamine (47 mL, 0.48 mmol, 10 equiv), followed by the addition of Pd(PPh$_3$)$_4$ under N$_2$. The reaction mixture was stirred at room temperature for 0.5 h. EtOAc (10 mL) was added, and the solution was quickly filtered through a short column of silica gel. The silica gel was washed with EtOAc (100 mL), and the solution was concentrated under reduced pressure. The residue was purified by flash column chromatography using EtOAc: hexanes (1:2) as the eluent and dried in vacuo to give 7-p-nitrobenzyloxycarbonyl-10-DAB as a colorless solid: yield, 28 mg (93%). [α]$_{Hg}$ −38° (CHCl$_3$, c=0.48); $^1$H NMR (400 MHz, CDCl$_3$) δ 1.06(s, 3 H, Me16), 1.09(s, 3 H, Me17), 1.55(s, 1 H, 1-OH), 1.86(s, 3 H, Me19), 2.01(ddd, J=14.4, 10.7, 2.0 Hz, 1 H, H6b), 2.03(d, J=5.1 Hz, 1 H, 13-OH), 2.09(d, J=1.3, 3 H, Me18), 2.28(m, 2 H, H14a, H14b), 2.30(s, 3 H, 4-Ac), 2.62(ddd, J=14.4, 9.5, 7.3 Hz, 1 H, H6a), 3.89(d, J=2.0 Hz, 1 H, 10-OH), 4.08(d, J=6.9 Hz, 1 H, H3), 4.20(d, J=8.4 Hz, 1 H, H20b), 4.34(d, J=8.4 Hz, 1 H, H20a), 4.88(m, 1 H, H13), 4.96(dd, J=9.5, 2.0 Hz, 1 H, H5), 5.19(d, J=13.3, 1 H, CHH'OC(O)), 5.26(d, J=13.3, 1 H, CHH'OC(O)), 5.36(dd, J=10.7, 7.3 Hz, 1 H, H7), 5.40(d, J=2.0 Hz, 1 H, H10), 5.64(d, J=6.9 Hz, 1 H, H2), 7.48(dd, J=8.1, 7.5 Hz, 2 H, benzoate, m), 7.52(d, J=8.7, 2 H, NO$_2$C6H$_4$), 7.61(tt, J=7.5, 1.3 Hz, 1 H, benzoate, p), 8.10(d, J=8.1, 1.3 Hz, 2 H, benzoate, o), 8.26(d, J=8.7, 2 H, N02C$_6$H$_4$) ppm. $^{13}$C NMR (75 MHz, CDCl$_3$) δ 10.5(Me (19)), 14.6(Me(18)), 19.4(4-Ac), 22.2, 26.4(Me16, Me17), 33.2(C(6)), 38.7(C(14)), 42.4(C(15)), 46.5(C(3)), 56.5(C (8)), 67.9, 68.3(C(13), OCH$_2$Ph-NO$_2$-p), 74.7, 75.2, 76.8(C (7), C(2), C(10), C(20)), 78.8(C(1)), 80.4(C(4)), 83.6(C(5)), 124.1, 128.4, 128.9, 130.3, 133.9 (OCH$_2$Ph-NO$_2$-p, benzoate), 135.0(C(11)), 142.4, 143.0 (OCH$_2$Ph-NO$_2$-p, C(12)), 154.2(OC(O)O), 167.3(benzoate), 171.1(4-Ac), 211.6(C(9))ppm.

EXAMPLE 9

Selective Esterification of the C-10 Hydroxyl of 10-DAB using the catalytic DyCl$_3$ reaction: A solution of butyric anhydride (0.55 mmol) in THF (1.32 ml) was added, under a nitrogen atmosphere, to a solid mixture of 10-DAB (30 mg, 0.055 mmol) and $DyCl_3$ (1.3 mg, 10 mol. % wrt 10-DAB). The resulting suspension was stirred at room temperature until judged complete by TLC (2:1 EtOAc/ Hexane). The reaction was diluted with EtOAc and washed three times with saturated $NaHCO_3$ solution. The combined bicarbonate washings were extracted three times with EtOAc, these combined organics were dried ($Na_2SO_4$) and the solvent evaporated. The crude product was triturated with hexanes and the mother liquors decanted away. Crystallization from EtOAc/hexanes yielded 10-butyryl-10-DAB identical to that isolated from the $CeCl_3$ catalysed reaction.

EXAMPLE 10

Selective Esterification of the C-10 Hydroxyl of 10-DAB using the catalytic $YbCl_3$ reaction: A solution of butyric anhydride (0.55 mmol) in THF (1.32 ml) was added, under a nitrogen atmosphere, to a solid mixture of 10-DAB (30 mg, 0.055 mmol) and $YbCl_3$ (1.3 mg, 10 mol. % wrt 10-DAB). The resulting suspension was stirred at room temperature until judged complete by TLC (2:1 EtOAc/ Hexane). The reaction was diluted with EtOAc and washed three times with saturated $NaHCO_3$ solution. The combined bicarbonate washings were extracted three times with EtOAc, these combined organics were dried ($Na_2SO_4$) and the solvent evaporated. The crude product was triturated with hexanes and the mother liquors decanted away. Crystallization from EtOAc/hexanes yielded 10-butyryl-10-DAB identical to that isolated from the $CeCl_3$ catalysed reaction.

In view of the above, it will be seen that the several objects of the invention are achieved.

As various changes could be made in the above compositions without departing from the scope of the invention, it is intended that all matter contained in the above description be interpreted as illustrative and not in a limiting sense.

What is claimed is:

1. A process for the silylation of a C(10) hydroxy group of a taxane, the process comprising treating the taxane with a silylamide or a bissilylamide to form a C(10) silylated taxane.

2. The process of claim 1 wherein the silylamide or bissilylamide corresponds to structures 6 or 7, respectively:

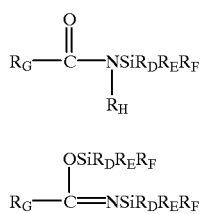

wherein $R_D$, $R_E$, $R_F$, $R_G$, and $R_H$ are independently hydrocarbyl, substituted hydrocarbyl, or heteroaryl.

3. The process of claim 2 wherein the taxane is treated with the silylamide or bissilylamide in the presence of an alkali metal base catalyst.

4. The process of claim 2 wherein the taxane is treated with the silylamide or bissilylamide in the presence of a catalyst selected from the group consisting of lithium amide catalysts.

5. The process of claim 1 wherein the silylamide or bissilylamide is selected from the group consisting of tri (hydrocarbyl)silyl-trifluoromethylacetamides and bis tri (hydrocarbyl)-silyltrifluoromethylacetamides, with the hydrocarbyl moiety being substituted or unsubstituted alkyl or aryl.

6. The process of claim 1 wherein the C(10) silylated taxane comprises a C(7) hydroxy group and the process additionally comprises treating the C(10) silylated taxane with an acylating agent to acylate the C(7) hydroxy group.

7. The process of claim 1 wherein the taxane treated with the silylamide or bissilylamide is 10-deacetyl baccatin III and the process additionally comprises treating the C(10) silylated taxane with an acylating agent to acylate the C(7) hydroxy group.

8. The process of claim 1 wherein the taxane has the structure:

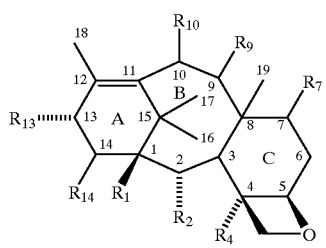

wherein $R_1$ is hydrogen, hydroxy, protected hydroxy, or together with $R_{14}$ or $R_2$ forms a carbonate;

$R_2$ is keto, —$OT_2$, acyloxy or together with $R_1$ forms a carbonate;

$R_4$ is —$OT_4$ or acyloxy;

$R_7$ is hydrogen, halogen, —$OT_7$, or acyloxy;

$R_9$ is hydrogen, keto, —$OT_9$, or acyloxy;

$R_{10}$ is hydroxy;

$R_{13}$ is hydroxy, protected hydroxy, keto, or

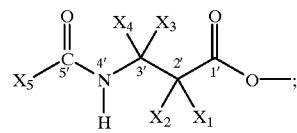

$R_{14}$ is hydrogen, —$OT_{14}$, acyloxy, or together with $R_1$, forms a carbonate;

$T_2$, $T_4$, $T_7$, $T_9$, and $T_{14}$ are independently hydrogen or hydroxy protecting group;

$X_1$ is —$OX_6$, —$SX_7$, or —$NX_8X_9$;

$X_2$ is hydrogen, hydrocarbyl, substituted hydrocarbyl, or heteroaryl;

$X_3$ and $X_4$ are independently hydrogen, hydrocarbyl, substituted hydrocarbyl, or heteroaryl;

$X_5$ is —$X_{10}$, —$OX_{10}$, —$SX_{10}$, —$NX_8X_{10}$, or —$SO_2X_{11}$;

$X_6$ is hydrocarbyl, substituted hydrocarbyl, heteroaryl, hydroxy protecting group or a functional group which increases the water solubility of the taxane derivative;

$X_7$ is hydrocarbyl, substituted hydrocarbyl, heteroaryl, or sulfhydryl protecting group;

$X_8$ is hydrogen, hydrocarbyl, or substituted hydrocarbyl;

$X_9$ is an amino protecting group;

$X_{10}$ is hydrocarbyl, substituted hydrocarbyl, or heteroaryl;

$X_{11}$ is hydrocarbyl, substituted hydrocarbyl, heteroaryl, —$OX_{10}$, or —$NX_8X_{14}$; and $X_{14}$ is hydrogen, hydrocarbyl, substituted hydrocarbyl, or heteroaryl.

9. The process of claim 8 wherein $R_1$ is hydroxy or together with $R_{14}$ or $R_2$ forms a carbonate;

$R_2$ is —$OCOZ_2$, —$OCOOZ_2$, or together with $R_1$ forms a carbonate;

$R_4$ is —$OCOZ_4$;

$R_9$ is hydrogen or keto;

$R_{13}$ is hydroxy, protected hydroxy, or

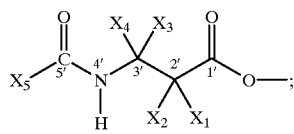

$R_{14}$ is hydrogen, hydroxy, protected hydroxy, or together with $R_1$ forms a carbonate;

$X_1$ is —$OX_6$ or —$NX_8X_9$;

$X_2$ is hydrogen, hydrocarbyl, or substituted hydrocarbyl;

$X_3$ and $X_4$ are independently hydrogen, hydrocarbyl, substituted hydrocarbyl, or heteroaryl;

$X_5$ is —$X_{10}$, —$OX_{10}$, or —$NX_8X_{10}$;

$X_6$ is a hydroxy protecting group;

$X_8$ is hydrogen, hydrocarbyl, or substituted hydrocarbyl;

$X_9$ is an amino protecting group;

$X_{10}$ is hydrocarbyl, substituted hydrocarbyl, or heteroaryl; and $Z_2$ and $Z_4$ are independently hydrocarbyl, substituted hydrocarbyl, or heteroaryl.

* * * * *

UNITED STATES PATENT AND TRADEMARK OFFICE
CERTIFICATE OF CORRECTION

PATENT NO. : 6,191,287 B1
DATED : February 20, 2001
INVENTOR(S) : Robert A. Holton, Zhuming Zhang and Paul A. Clarke It is certified that error appears in the above-identified patent and that said Letters Patent is hereby corrected as shown below:

Column 1,
Line 7, please change "60/081,265, filed Aug. 18, 1997" to read
-- 60/056,000, filed Aug. 18, 1997 --.

Column 6,
Lines 24-33, the first structure of "Scheme 4" should read:
--

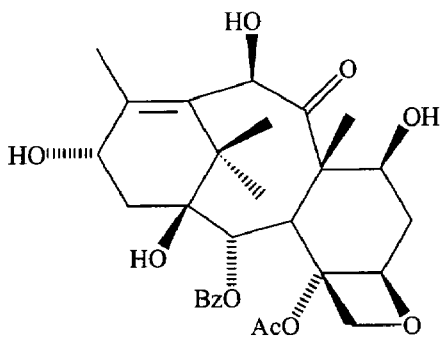

--

Column 7,
Line 19 "trifluoromethylacetamides" should read -- wherein $R_D$, $R_E$, $R_F$, $R_G$, and $R_H$ are independently hydrocarbyl, substituted hydrocarbyl, or heteroaryl. Preferably, the silylating agents are selected from the group consisting of tri(hydrocarbyl) silyl-trifluoromethylacetamides --.

Column 8,
Lines 15-20, Scheme 7, the portion that reads "THF, 0° C., 15 ml n 95%" should read -- THF, 0° C., 15 min 95% --.

Column 9,
Lines 45-53, the second structure of Scheme 9, the portion that reads "OAlloc" should read -- OAlloc --.

Column 14,
Lines 5-9, Scheme 17, the portion that reads "I ml dazole" should read
-- Imidazole --.
Lines 28-32, Scheme 18, the portion that reads "I ml dazole" should read -- Imidazole --.
Lines 52-55, Scheme 19, the portion that reads "(Me)₂IPrSICI" should read
-- (Me)$_2$IPrSiCl --.

UNITED STATES PATENT AND TRADEMARK OFFICE
CERTIFICATE OF CORRECTION

PATENT NO.    : 6,191,287 B1
DATED         : February 20, 2001
INVENTOR(S)   : Robert A. Holton, Zhuming Zhang and Paul A. Clarke It is certified that error appears in the above-identified patent and that said Letters Patent is hereby corrected as shown below:

Column 16,
Lines 12-14, Scheme 22, the portion that reads "THF, R.T. Bh. 92%" should read -- THF, R.T. 8h. 92% --.

Columns 17-18,
Scheme 23, the portion that reads "(2)(Me)$_2$PhSICl" should read -- (2)(Me)$_2$(PhSiCl --.

Column 24,
Line 16, "P10" should read -- $P_{10}$ --.
Line 20, "-(C=O)NR$^c$" should read -- -(C=O)NR$_c$ --.

Signed and Sealed this

Twenty-seventh Day of May, 2003

JAMES E. ROGAN
*Director of the United States Patent and Trademark Office*